US009951148B2

(12) United States Patent
Helin et al.

(10) Patent No.: US 9,951,148 B2
(45) Date of Patent: Apr. 24, 2018

(54) METHOD FOR ISOLATION OF POLYSACCHARIDES

(75) Inventors: Jari Helin, Helsinki (FI); Jean Hypolites Koek, Vlaardingen (NL)

(73) Assignee: NutriLeads B.V., Rockanje (NL)

( * ) Notice: Subject to any disclaimer, the term of this patent is extended or adjusted under 35 U.S.C. 154(b) by 58 days.

(21) Appl. No.: 14/114,461

(22) PCT Filed: Apr. 27, 2012

(86) PCT No.: PCT/NL2012/050292
§ 371 (c)(1),
(2), (4) Date: Oct. 28, 2013

(87) PCT Pub. No.: WO2012/148277
PCT Pub. Date: Nov. 1, 2012

(65) Prior Publication Data
US 2014/0056946 A1 Feb. 27, 2014

(30) Foreign Application Priority Data
Apr. 29, 2011 (EP) .................................. 11164258

(51) Int. Cl.
*A61K 36/24* (2006.01)
*C08B 37/00* (2006.01)
*A61K 31/732* (2006.01)
*A61K 36/748* (2006.01)
*A61K 36/896* (2006.01)
*A61K 36/8966* (2006.01)
*A61K 36/074* (2006.01)
*A61K 36/344* (2006.01)
*A61K 36/41* (2006.01)
*A61K 36/481* (2006.01)
*A61K 36/539* (2006.01)
*A23L 33/105* (2016.01)

(52) U.S. Cl.
CPC .......... *C08B 37/006* (2013.01); *A23L 33/105* (2016.08); *A61K 31/732* (2013.01); *A61K 36/074* (2013.01); *A61K 36/24* (2013.01); *A61K 36/344* (2013.01); *A61K 36/41* (2013.01); *A61K 36/481* (2013.01); *A61K 36/539* (2013.01); *A61K 36/748* (2013.01); *A61K 36/896* (2013.01); *A61K 36/8966* (2013.01); *C08B 37/0045* (2013.01); *C08B 37/0048* (2013.01)

(58) Field of Classification Search
None
See application file for complete search history.

(56) References Cited

U.S. PATENT DOCUMENTS 3,971,858 A 7/1976 Collier et al.
5,567,462 A 10/1996 Ehrlich
6,432,454 B1 8/2002 Shan et al.
7,691,986 B2 4/2010 Ni et al.
2002/0187209 A1* 12/2002 Ko ..................... A61K 36/258
424/728
2007/0049551 A1 3/2007 Eliaz

FOREIGN PATENT DOCUMENTS

| EP | 0035643 A1 * | 9/1981 | |
|---|---|---|---|
| JP | 2009-165452 | 7/2009 | |
| UA | 75734 C2 | 11/2005 | |
| WO | WO-99/19365 A1 | 4/1999 | |
| WO | WO-2004/020472 A2 | 3/2004 | |
| WO | WO 2005095463 A1 * | 10/2005 | ........... A61K 31/732 |
| WO | WO-2007/128578 A1 | 11/2007 | |
| WO | WO-2009/071425 A1 | 6/2009 | |

OTHER PUBLICATIONS

Chesson, Andrew et al., "Pectic polysaccharides of mesophyll cell walls of perennial ryegrass leaves", Phytochemistry (Oxford), vol. 38, No. 3, 1995, pp. 579-583.
Kratchanova, Maria et al., "Compsition and properties of biologically active pectic polysaccharides from leek (*Allium porrum*)", Journal of the Science of Food and Agriculture, vol. 90, No. 12, Sep. 2010, pp. 2046-2051.
Renard CMGC et al. "Studies on apple protopectin: I. Extraction of insoluble pectin by chemical means", Carbohydrate Polymers, Applied Science Publicshers, Ltd. Barking, GB, vol. 12, No. 1, Jan. 1, 1990, pp. 9-25.
Deng, et al. "Selective chemical depolymerization of rhamnogalacturonans", Carbohydrate Research (2006) vol. 341, pp. 474-484.
Diaz et al., "Nonenzymatic Degradation of Citrus Pectin and Pectate during Prolonged Heating: Effects of pH, Temperature, and Degre of Methyl Esterification", J. Agric Food Chem., (2007) vol. 55, pp. 5131-5136.
Dobias, et al. "Deesterification of Apple Pectin in an Ammoniacal Medium" Sbornik Vysoke Skoly Chemicko-Technologicke v Praze [Scientific Papers of the Prague Institute of Chemical Technology](1986), E 60, 51-59.

(Continued)

*Primary Examiner* — Amy L Clark
(74) *Attorney, Agent, or Firm* — Gilberto M. Villacorta; Sunit Talapatra; Foley & Lardner LLP

(57) ABSTRACT

The invention relates to a method for production of a preparation from a vegetable material, said preparation being enriched in a polysaccharide with a backbone comprising rhamnogalacturonan-I cores, said method comprising the steps:
  mixing the vegetable material with a polar alcoholic solvent; and
  separating a solid residue obtained in step a) from the solvent; and
  mixing the solid residue obtained in step b) with a buffered aqueous solution having a pH between 7 and 8.
Also provided is a preparation containing rhamnogalacturonan-I pectins that can be obtained by this method and the use of such a preparation to modulate immune response.

21 Claims, 3 Drawing Sheets

(56) References Cited

OTHER PUBLICATIONS

Ele Ekouna, et al. "Chemical characterization of pectin from green tea (*Camellia sinesis*)", Carbohydrate Polymers (2011) vol. 83, p. 1232-1239.

Fischer, et al. "Changes in the pectic substances of apples during development and postharvest ripening. Part 2: Analysis of the pectic fractions", Carbohydrate Polymers, (1994) vol. 25, p. 167-175.

Katayama, et al. "Localization of mucilaginous polysaccharides in mulberry leaves" Protoplasma (2008) vol. 233, p. 157-163.

Lin, et al. "Isolation and viscometric characterization of hydrocolloids from mulberry (*Morus alba* L.) leaves" Food Hydrocolloids (2009) vol. 23, p. 840-848.

May, "Industrial Pectins: Sources, Production and Applications", Carbohydrate Polymers (1990) vol. 12, pp. 79-99.

Ralet et al., "Mass spectrometry for pectin structure analysis", Carbohydrate Research,(2009) vol. 344, pp. 1798-1807.

Redgwell, et al. "Role of pectic polysaccharides in structural integrity of apple cell wall material", European Food Research and Technology (2008) vol. 227, p. 1025-1033.

Ryden, et al. "Cell-wall polysacchraides and glycoproteins of parenchymatous tissues of runner bean (*Phaseolus coccineus*)", Biochemical Journal (1990) vol. 269, p. 393-402.

Sila, et al. "beta-Elimination of Carrot Pectin: Towards a Better Understanding of Carrot Texture During Thermal Processing", Commun. Appl. Biol. Sci.—Ghent University (2005) vol. 70/2, pp. 19-22.

Sila, et al., "Pectins in Processed Fruits and Vegetables: Part II—Structure-Function Relationships", Comprehensive Reviews in Food Science and Food Safety (2009) vol. 8, 86-104.

Westereng et al., "Release and characterization of single side chains of white cabbage pectin and their complement-fixing activity", Mol. Nutr. Food Res. (2009) vol. 53, p. 780-789.

Xia, et al. "Structural Analysis of Polysaccharide SJB from Mulberry Leaves and Its Inhibitory Activities of Protein Tyrosine Phosphatase-1 B", Chemical Journal of Chinese Universities (2008) vol. 29, p. 2205-2208. [Abstract].

Zhu, et al. "Characterization of cell wall polysaccharides from the medicinal plant *Panax notoginseng*", Phytochemistry (2005) vol. 66, p. 1067-1076.

\* cited by examiner

METHOD FOR ISOLATION OF POLYSACCHARIDES

This application is the National Phase of PCT/NL2012/050292 filed Apr. 27, 2012, which claims priority to European Patent Application No. 11164258.3 filed Apr. 29, 2011, the disclosures of which are hereby incorporated by reference in their entirety.

The present invention relates to a method for isolation of polysaccharides that can be used to modulate immune response.

Pectin is a complex mixture of colloidal polysaccharides found in the primary cell walls of both monocotyledons (monocots) and dicotyledons (dicots) in the plant kingdom. Together with cellulose, hemicellulose and proteins they constitute the plant cell walls. It is characterized by the presence of rhamnosyl, galacturonyl acid, arabinosyl, and galactosyl residues as the main components, and at least occasionally xylosyl, mannosyl, glucosyl and apiosyl residues. Traditionally, pectin is known for its gelling and viscosifying properties utilized in industrial and household preparations of jellies, jam, and marmalade and it is widely used for its thickening and viscosifying properties.

Pectin is generally regarded to be poly-D-galacturonic acid (homogalacturonan), wherein the galacturonyl acid moieties are linked via alpha(1-4) linkages. The carboxyl group of a galacturonyl acid residue may be esterified with methanol, to create high methoxy and low methoxy pectins. The degree of methyl esterification influences the gelling behaviour of pectin. The usual distinction is between LM-pectin (low methoxyl, less than 50% of the carboxyl groups esterified), and HM-pectin (high methoxyl, more than 50% of the carboxyl groups esterified). LM-pectin forms gels upon the addition of divalent cations, especially calcium. HM-pectin does not require cations to form gels. Additionally the galacturonic acid may be acetylated, in addition to the presence of methyl esters. In that case one of the hydroxyl groups 2-OH and 3-OH positions are substituted by esterification to yield the acetates. Acetylation generally prevents gel-formation but increases the stabilising and emulsifying effects of pectin.

Pectic polysaccharide is regarded to be a heterogeneous group of polysaccharides including various amounts of various components sometimes present or absent such as (i) homogalacturonan (HG) as described above, (ii) xylogalacturonan (XGA), (iii) rhamnogalacturonan-I backbone, encompassing arabinan and arabinogalactan I and II sidechains (RG-I), and (iv) rhamnogalacturonan-II (RG-II) (Ralet et al., Carbohydrate Research, vol. 344, 2009, p. 1798-1807; Sila D. N. et al., Comprehensive Reviews in Food Science and Food Safety, 2009, vol. 8, 86-104). Pectic polysaccharide composition and fine structure vary widely depending on the plant source and the extraction conditions applied. The homogalacturonan core can have a length of up to about 100 consecutive D-GalA residues. The RG-I core containing the side chains is usually called the 'ramified region' or 'hairy region', while the homogalacturonan core (between two RG-I cores) is not typically substituted with oligosaccharides.

Rhamnogalacturonans are a group of closely related cell wall pectic polysaccharides that contain a backbone of the repeating disaccharide:

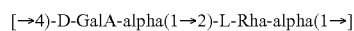

(which can also be represented as: [-4)-D-GalA-alpha(1-2)-L-Rha(p)-alpha(1-])

Rhamnogalacturonan-I (RG-I) is referred to as regions with 30-40 repeats of GalA and rhamnose (Rha) pairs [Westereng et al., Mol. Nutr. Food Res. 2009, vol. 53, p. 780-789], with varying numbers of Rha residues. The GalA residues are linked to the Rha residues via the 1 and 4 positions, while the Rha residue is linked to the GalA residue via the anomeric and 2-OH positions. In general about 20-80% of the Rha residues is branched at the 4-OH position (depending on the plant source and the method of isolation), with neutral and acidic side chains (or 4-OH position). These side chains consist mainly of Ara and Gal residues linked in various manners, constituting polymers known as arabinogalactan I (AG-I) and/or AG-II. AG-I is composed of a beta-(1,4)-linked D-Gal backbone with substitutions at 3-OH of alpha-L-arabinosyl groups; the Gal backbone can have interspacing alpha(1,5)-L-Ara units. AG-II consists of highly ramified galactan with predominantly interior beta(1,3)-linked D-Galp with substitutions of short (1,6)-linked chains exteriorly. The latter has further attachments of (1,3)- and/or alpha(1,5)-linked L-Ara. The oligosaccharide side chains may be linear or branched, and some of these side chains may be terminated with alpha-L-fucosides, beta-D-glucuronides, and 4-O-methyl beta-D-glucuronyl residues.

Some of the pectic polysaccharides are known for their modulation of the immune system upon administration. U.S. Pat. No. 6,432,454 B1 discloses a procedure for isolation of immuno-activating polysaccharides. This procedure is specific described for ginseng and gives a yield of about 10%. The active polysaccharides have a relatively high molecular weight.

WO 2009/071425 A1 discloses a method to isolate immuno-activating polysaccharides from plants of the Asclepiadoideae subfamily, more in particular from *Hoodia* species. The method involves cutting vegetable material in pieces, and washing the material with a methanol-water mixture. The material which was insoluble in the methanol was further mixed with and heated in an ethanol-water mixture. Subsequently the material which was insoluble in the ethanol was mixed with demineralised water and cooked for 3 hours. The supernatant contained the polysaccharides of interest.

Ele Ekouna J.-P. et al. (Carbohydrate Polymers, 2011, vol. 83, p. 1232-1239) disclose a method for isolation of polysaccharides (pectin) from green tea (*Camellia sinensis*).

A disadvantage of these methods is that the yield of the immuno-modulating polysaccharides is relatively low (5 to 10%).

Pectins are usually extracted from vegetable materials using acid conditions or applying chelators to facilitate removal from the matrix, for example as in May C. D. (Carbohydrate Polymers 1990, vol. 12, 79-99).

Hot water extraction and/or acidic conditions have the disadvantage that gels are formed in the extraction process, and this allows only for dilute conditions which lowers the reactor use efficiency increasing processing costs. Another disadvantage is that by applying the usual acid conditions the yields are comparable or lower than by only hot water extraction, probably due to gelling problems. Moreover due to heating beta-elimination may occur, which is a base-catalysed splitting of the homo-polygalacturonic acid chains into smaller parts. Beta-elimination increases when the temperature is increased, and at pH>4.5 (Sila D. N. et al., Comprehensive Reviews in Food Science and Food Safety, 2009, vol. 8, 86-104). As in most instances pectin is required for its structuring properties, the normal tendency is to prevent or limit the beta-elimination process in order to retain a relatively long molecule of homo-polygalacturonic acid stretches. Chain breakage of pectins occurs easily for esterified but not for de-esterified fragments due to the nature of the base induced beta-elimination, requiring a carboxymethylester group in the alfa position (Diaz J. V. et al., Agric Food Chem., 2007, vol. 55, 5131-5136).

WO 2004/020472 A2 describes a process to treat vegetable material containing pectin, by heating to a temperature below 90° C. and pH 3.2-3.9 to inactivate naturally present pectin esterase. This way minimal de-esterification of the pectin occurs.

In order to overcome the disadvantages of acidic conditions, pectin extraction and identification of the composition of the extracted polysaccharides have been carried out at neutral to alkaline conditions.

Sila D. N. et al. (Commun Agric. Appl. Biol. Sci. 2005, vol. 70(2), 19-22) disclose that in pectin processing aqueous sodium carbonate solutions may be used at high temperature (90-110° C.), in order to induce fragmentation of the main chain to reduce the gelling. The fragmentation will lead to reduction of the molecular weight of the polysaccharides. Beta-elimination is strongly favoured by increasing pH (from 3.5 to 9), due to the presence of methyl ester groups. By pre-processing de-esterification occurs to decrease the methyl-ester content, leading to decrease of the water extractable amount of pectin while increasing the carbonate extractable, non-esterified amount of pectin which is resistant to beta-elimination.

Dobias J. et al. (Sbornik Vysoke Skoly Chemicko-Technologicke v Praze 1986, E60, 51-59) disclose that de-esterification of apple pectin can be achieved by applying cold alkali (ammonia) to control gelling properties, by hydrolyzing the methyl esters.

JP 2009-165452 A describes the use of hot spring water or bicarbonate solution for extraction of pectin, during a time period of 5-150 minutes, instead of using an acidic step at pH 1.5-2.5 during 30 minutes to several hours.

UA75734C discloses a process for the production of pectin from apple-tree leaves, wherein a 2% sodium bicarbonate solution in combination with 2M sodium hydrate is used, hence a high pH is applied in this process.

U.S. Pat. No. 3,971,858 describes the use of ammonia or ammonium bicarbonate for extraction of solids from tea leaves for the preparation of tea extracts to produce soluble instant tea. Due to the high temperature preferred (100° C.) it is to be expected that the ammonium bicarbonate is converted into carbondioxide, water and ammonia and it can be derived that ammonia is the active ingredient responsible for the increased yield to 30%.

Deng C. et al. (Carbohydrate Research, 2006, vol. 341, 474-484) disclose depolymerisation of rhamnogalacturonans by first methyl esterification and then cleavage of the galacturonic acid residues in pectic polysaccharides by beta-elimination. The latter step is done at pH 7.3 and 125° C. in 0.2 M sodium borate. Fragments that were obtained included low molecular weight oligosaccharides (having a molecular weight up to about 1300 Da) originating from the RG-I core.

Lin H. Y. et al. (Food Hydrocolloids, 2009, vol. 23, p. 840-848) disclose the isolation of hydrocolloids from mulberry (*Morus alba* L.) leaves. The leaves were extracted using a 0.14M sodium bicarbonate solution at 95° C. during 4 hours. The extract contained mainly carbohydrates with a high level of uronic acid, 28-33% based on dry weight. The neutral sugar compositions of the extract constituted mainly of rhamnose (23-27 molar %), arabinose (20-21 molar %), galactose (23-24 molar %), glucose (21-26 molar %), xylose (6-7 molar %), and trace amount of mannose (<0.3 molar %). Based on the high average molecular weight of the carbohydrates obtained (about 6100 kDa and 6600 kDa) and the insensitivity of the polysaccharides for divalent cations (the viscosity of a solution of the extract does not increase upon addition of cations), it can be concluded that the polysaccharide that is extracted here is different from a typical rhamnogalacturonan-I structure, due to its high glucose level, very high molecular weight, and the uronic acids are not specified to be galacturonic acid. Katayama H. et al. (Protoplasma, 2008, vol. 233, p. 157-163) describe that acidic mucilaginous polysaccharides are located between the plasma membrane and the cell wall, and are not part of the plant cell wall.

Xia W. et al. (Chemical Journal of Chinese Universities, 2008, vol. 29, p. 2205-2208) disclose the extraction of polysaccharides from mulberry leaves, using a solution of NaOH in water (0.5M, highly alkaline conditions, 4° C., pH>13). The polysaccharides had an average molecular weight of 54 kDa, and were effective in lowering blood glucose levels.

Redgwell R. J. et al. (European Food Research and Technology, 2008, vol. 227, p. 1025-1033) disclose the depletion of pectin from apple cell wall material using an extraction step with sodium carbonate solution. The use of the sodium carbonate leads to the extraction of pectic polysaccharide from the primary cell wall, and the polysaccharides are de-esterified by the alkaline pH. The authors do not provide details on the structures of obtained molecules.

Zhu et al. (Phytochemistry, 2005, vol. 66, p. 1067-1076) disclose isolation of rhamnogalacturonan-I polysaccharide from *Panax notoginseng*, which is a medicinal plant used in China. A first extraction step is done using methanol, and the alcohol insoluble residue is subjected to extraction using acetic acid and phenol. Subsequently the residue from that step is treated in hot water (100° C. during 30 minutes). This step probably will lead to beta-elimination of pectic polysaccharides, due to the high temperature. Next the residue is extracted using a solution of sodium carbonate (supplemented with sodium borohydride ($NaBH_4$) and sodium azide ($NaN_3$)). In a first step the extraction is performed overnight at 4° C., at a pH of at least 11 (0.05 M $Na_2CO_3$), followed by a second step during 6 hours at room temperature. The first step will lead to demethylation of galacturonic acid-methyl esters. The second step at the higher temperature then is to solubilise the de-esterified pectic polysaccharide. The authors do not provide details on the molecular weight of RG-I fragments, they are expected to be low based on the alkali conditions in the extraction step in the first overnight step at 4° C., at which degradation of the molecules will occur. This leads to the assumption that the method applied here is suitable for determining structures which were present in the raw materials, while it is not suitable to extract polysaccharides having a high molecular weight for stimulating immune response. Additionally the fractions obtained only contain very low amounts of RG-I (3 to 5%).

Ryden P. (Biochemical Journal, 1990, vol. 269, p. 393-402) disclose extraction of cell-wall polysaccharides from runner bean (*Phaseolus coccineus*), using a solution of sodium carbonate with sodium borohydride. Two extraction steps are applied: 0.05M $Na_2CO_3$ for 20 h at 1° C., and subsequently 0.05M $Na_2CO_3$ for 2 h at 20° C. The authors indicate that the major problem is to study the structure of cell wall polysaccharides with minimal degradation upon extraction, implicitly indicating that at these conditions the polysaccharides degrade. No indication about molecular weight of obtained materials is provided.

Fischer M. et al. (Carbohydrate Polymers, 1994, vol. 25, p. 167-175) disclose the isolation of pectic polysaccharides using two extraction steps, the first with trans-1,2-diaminocyclohexane-N,N,N',N'-tetraacetic acid (CDTA), and as a second step a double sodium carbonate extraction. The double extraction step with sodium carbonate comprises first 0.05M $Na_2CO_3$ at 1° C. for 16 h (minimising beta-elimination), and second 0.05M $Na_2CO_3$ at 20° C. for 3 h. The pH at this step will be at least 10, due to the high carbonate concentration.

SUMMARY OF THE INVENTION

The prior art indicates that treating vegetable materials at alkaline conditions will lead to isolation and fragmentation of polysaccharides to relatively low molecular weights. By applying these alkaline conditions immuno-stimulating polysaccharides are not extracted. Additionally, if larger polysaccharides would need to be obtained, long extraction times at low temperatures are required, to minimise beta-elimination, and still high risk of fragmentation of polysaccharides. This decreases the efficiency of an extraction vessel dramatically. Hence there is a need to increase the efficiency of extraction in order to obtain polysaccharides from vegetable materials which have an immuno-modulating effect, in particular to obtain polysaccharides which contain rhamnogalacturonan-I cores and have a molecular weight which is active in stimulation of the immune system.

The molecular weight should be high enough to still influence the immune system, while on the other hand the polysaccharide should not or only limitedly gel upon extraction, in order to prevent difficult processing and consequently decrease yield of the extraction process. Moreover large-scale implementation of the procedures has shown that the desired products not in all cases have a consistent biological activity, hence achieving reproducible results is essential.

We now found that upon applying high temperatures at relatively short time the use of a buffered aqueous solution having a pH between 7 and 8 allowed to isolate the polysaccharides containing both RG-I cores and RG-I core and polygalacturonic acid stretches in the right ratio to obtain an immuno-modulating effect, and having a molecular weight between 40 kDa and 2,000 kDa. Moreover, the yield was higher than upon using, neutral or acidic conditions. Also the processing was easier due to the absence of gelling even for the vegetable sources which upon extraction with hot water or acid gave gelling at the same concentrations used. This allows for performing the extraction at higher concentrations, and hence achieving a higher efficiency in extraction.

Accordingly in a first aspect the present invention provides a method for production of a preparation from a vegetable material enriched in a polysaccharide,
wherein the backbone of the polysaccharide comprises rhamnogalacturonan-I cores and optionally alpha(1,4)-linked homo-galacturonic acid stretches,
wherein the molar ratio of galacturonyl acid residues to rhamnosyl residues in the backbone of the polysaccharide ranges from 30:1 to 1:1,
and wherein the polysaccharide has a molecular weight between 40 kDa and 2,000 kDa, comprising the steps:
a) mixing the vegetable material with a polar alcoholic solvent, preferably ethanol; and
b) separating a solid residue obtained in step a) from the solvent; and
c) mixing the solid residue obtained in step b) with a buffered aqueous solution having a pH between 7 and 8; and
d) optionally separate the solid residue from the aqueous solution as obtained from step c); and
e) optionally purify the aqueous solution from step d) to yield the polysaccharide.

In a second aspect the present invention provides a preparation obtainable by the method according to the first aspect of the invention.

In a third aspect the present invention provides a preparation obtained from the method according to the first aspect of the invention or a preparation according to the second aspect of the invention for use as a medicament.

DETAILED DESCRIPTION

Unless defined otherwise, all technical and scientific terms used herein have the same meaning as commonly understood by one of ordinary skill in the art.

All percentages, unless otherwise stated, refer to the percentage by weight.

In case a range is given in the context of the present invention, the indicated range includes the mentioned endpoints.

Abbreviations: kDa—kilo Dalton; Gal—D-Galactose; GalA—D-Galacturonic acid; Rha—L-Rhamnose; Ara—L-Arabinose; Fuc—L-Fucose; Glc—D-Glucose; GlcA—D-Glucuronic acid. The L- and D-forms of these monomers as indicated here also apply to the monomers as indicated in the rest of this specification (which may not be abbreviated but written in full).

The term "pectic polysaccharides" encompasses homogalacturonans, xylogalacturonans, rhamnogalacturonan-I pectins, rhamnogalacturonan-II pectins and combinations thereof.

The term "rhamnogalacturonan-I pectins" or "RG-I pectins" refers to pectic polysaccharides that comprise one or more rhamnogalacturonan-I cores.

The term "rhamnogalacturonan-I core" or "RG-I core" refers to linear stretches of 10-200, preferably 30-40 repeats of galacturonic acid (GalA) and rhamnose (Rha) pairs, wherein the GalA residues are linked to the Rha residues via the 1 and 4 positions, while the Rha residue is linked to the GalA residue via the anomeric and 2-OH positions, i.e. alternating alpha(1→4)-galacturonyl-alpha(1→2)-rhamnosyl residues.

Vegetable material: in the context of the present invention a vegetable material refers to material from plant origin, and this material may origin from a vegetable or from a fruit (as commonly understood in kitchen or recipe context).

Bicarbonate refers to the anion $HCO_3^-$, which can be added to a preparation in the form of a salt, such as sodium bicarbonate or potassium bicarbonate.

Immune Response

By the term 'modulating immune response' as used herein, is meant that the activity or capacity of the immune system to defend the body is modulated. This may relate to immuno-stimulation or immuno-suppression. The primary task of the immune system is to protect against pathogens such as fungi, bacteria, viruses, protozoa and parasites. In this context, modulating immune response preferably means stimulation of the immune response. Suitably, stimulation of the immune response contributes to an enhanced natural defence of the human body. On the other hand, the immune system sometimes mounts an immune response against harmless substances, like house mite, dust or pollen, resulting in allergy. In addition, many physiological disorders, like hypercholesterolemia and obesity, result in a low-grade inflammatory status Immune modulation in the context of abnormal immune responses, like allergy or (chronic) inflammation, means dampening or counteracting the hypersensitivity immune response. The present invention not only relates to the primary task of the immune system, but also to this second 'abnormal' immune response.

Several assays can be used to identify components that could modify immunity. Here we use of phagocytic and natural killer (NK) cells to aid the identification of immunostimulating compounds as these cells are part of the innate immune system, which is a rapidly activated non-specific first line of defence against pathogens.

Phagocytic cells such as neutrophils, monocytes and macrophages can generate reactive oxygen species (ROS) to kill pathogens such as fungi and bacteria. The effect of ingredients on phagocytosis activity can be measured ex vivo with fresh blood of healthy human volunteers after incubation with FITC-labelled *E. coli* bacteria. The percentage of phagocytosing cells in the granulocyte population can be determined by flow cytometry. The results are typically normalized to the effect of lipo-polysaccharide (LPS), which is a well known potent immunostimulating reference compound. Suitably, a normalized percentage phagocytosing granulocytes of more than 40% is regarded as a significant immune stimulating effect.

NK cells can kill target cells that have lost or express insufficient amounts of MHC class I, a frequent event in tumor- or virus-infected cells. The effect of ingredients on NK cell activity can ex vivo be measured with peripheral blood mononuclear cells (PBMC) isolated from fresh blood of healthy human volunteers. After pre-incubation of the PBMCs with the ingredient, pre-labelled K562 target cells are usually added and after subsequent incubation, propidium iodide can be added for detection of dead cells. The percentage of dead target cells can be determined with flow cytometry. The results are typically normalized to the effect of interleukin-2 (IL-2), which is a well known potent NK cell stimulating reference compound. Suitably, a normalized % NK cell activity of more than 17% is regarded as a significant immune stimulating effect.

Method for Production of Preparation from Vegetable Material

In a first aspect the present invention provides a method for production of a preparation from a vegetable material enriched in a polysaccharide, wherein the backbone of the polysaccharide comprises rhamnogalacturonan-I cores and optionally alpha(1,4)-linked homo-galacturonic acid stretches, wherein the molar ratio of galacturonyl acid residues to rhamnosyl residues in the backbone of the polysaccharide ranges from 30:1 to 1:1, and wherein the polysaccharide has a molecular weight between 40 kDa and 2,000 kDa, comprising the steps:
a) mixing the vegetable material with a polar alcoholic solvent, preferably ethanol; and
b) separating a solid residue obtained in step a) from the solvent; and
c) mixing the solid residue obtained in step b) with a buffered aqueous solution having a pH between 7 and 8; and
d) optionally separate the solid residue from the aqueous solution as obtained from step c); and
e) optionally purify the aqueous solution from step d) to yield the polysaccharide.

The method according to the invention is used for the production of an extract that is enriched in a polysaccharide as defined. The polysaccharide can be used to modulate immune response when ingested, inhaled or injected (preferably the latter two when used as adjuvant).

Plants that are suitable as starting material for extraction of the polysaccharides according to the present invention include any plant, but especially preferred are edible plants or plant organs, as described by the general term 'fruit and vegetables'. A vegetable is a plant that is cultivated for an edible part, such as the root of a beet, the leaf of spinach, or the flower buds of broccoli or cauliflower. A vegetable is generally seen as any savory or non- or low-sweetness plant product. Usually in culinary context the term vegetable excludes sweet fruits, seeds, nuts, grains, and herbs and spices. The definition of fruit depends on whether the term is used in culinary or botanical context. In culinary terms, fruit is usually a sweet tasting plant reproduction organ, like an apple, or strawberry. Some plant parts that are considered to be fruits in botanical sense, are seen as vegetables in culinary context, because they are not (or less) sweet, for example cucumber and tomato.

The organ of the plants which may serve as source of the preparation according to the invention depend on the actual species which is utilised as source of the polysaccharides. These organs may be any part of species, such as leaves (defined as the plant organ specialised for photosynthesis), including needles; flowers and flower heads; buds; seeds; pods; fruits; berries, tubers and roots, and the stem including the bark. For example, the following organs of the preferred species are preferred as source to obtain the polysaccharides using the method of the invention.

*Daucus carota* subsp. *sativus* (carrot): the root.
*Malus domestica* (apple): the fruit, especially the skin of the fruit.
*Capsicum annuum* (bell pepper or red or green pepper, or paprika): the fruit. Especially preferred is red bell pepper.

In order to facilitate extraction of polysaccharides comprising RG-cores, it is preferred to employ a vegetable material that has been treated to destruct the cell walls. Examples of treatments that can suitably be used to destruct cell walls contained in the vegetable materials include grinding, milling, cutting, osmolysis, freeze-thaw cycling, vacuum disruption, cooking and enzyme treatments. Naturally these techniques can also be used in combination. When enzyme treatment is used to destruct cell walls, care should be taken not to degrade the pectic polysaccharides that the present method aims to isolate. Thus, the enzyme preparation should have very little or no pectinase activity. Enzymes that may be used to degrade the cell walls include cellulases, proteases, amylases and combinations thereof.

The vegetable material that is mixed with the polar alcoholic solvent can dried or fresh plant material. Preferably, the plant material is dried plant material, e.g. plant material having a water activity of less than 0.9, even more preferably of less than 0.6 and most preferably of less than 0.5.

The polysaccharide that is obtained by the method of the invention may comprise one RG-I core which may be flanked at one or two of its sides by one or two homogalacturonic acid stretches. Alternatively, the polysaccharides may contain alternating RG-I fragments and homogalacturonic acid stretches.

Vegetable materials especially suitable as source of the preparation according to the invention comprise apple, carrot, bell pepper, or combinations thereof. Other sources may be crops like tomato, onion, herbs and spices, ginseng, and tea leaves (*Camellia sinensis*).

Generally, plant-based polysaccharides consist of large insoluble polymers, like cell wall components (e.g. cellulose), small soluble oligosaccharides, like monomers (e.g.

glucose) and dimers (e.g. cellobiose), and large soluble polysaccharides. Hence, prior to preparing the buffered aqueous extract, the vegetable material is mixed with a polar alcoholic solvent, preferably ethanol, preferably during a period of between 15 minutes and 6 hours. By this step a), small organic molecules like mono- and disaccharides, small organic acids and their metal salts, amino acids and oligopeptides, polyphenols, color contributing molecules like carotenoids, anthocyanes and chlorophyll, and fatty substances like glycerides, cholines, phospholipids and steroids are removed, in order to increase the relative content of polysaccharides in the vegetable material which does not dissolve in the solvent.

The polar alcoholic solvent employed in step a) advantageously is a C1-4 alcohol. Even more preferably, the polar alcoholic solvent is selected from ethanol, iso-propanol, methanol and combinations thereof. Most preferably, the polar alcoholic solvent is ethanol.

Preferably in step a) the vegetable material is mixed with an ethanol/water mixture, e.g. a mixture of 50% to 95% ethanol and water, more preferably a mixture of 70% to 85% ethanol and water, and most preferably a mixture of 70% to 80% ethanol and water.

According to another preferred embodiment, the vegetable material is mixed with a total amount of the polar alcoholic solvent that is at least 5 times, more preferably at least 8 times and most preferably at least 12 times higher than the dry weight of the vegetable material, preferably divided over two or more wash steps. The mixing of the vegetable material with the polar alcoholic solvent and the subsequent separation of solid residue is advantageously carried out as a sequence of washing steps, e.g. by again mixing the solid residue obtained form step b) with polar alcoholic solvent and separating the solid residue. This cycle may be repeated several times before the solid residue is mixed with the buffered aqueous solution in step c). As a matter of fact it is preferred that the present method employs at least 2, even more preferably at least 3 of these washing steps before the solid residue is mixed with the buffered aqueous solution.

Preferably the temperature in step a) is between 30° C. and 100° C. at atmospheric pressure, preferably between 50° C. and 95° C., preferably between 60° C. and 80° C. Preferably, this step a) takes place during a period of between 15 minutes and 6 hours, preferably between 1 and 3 hours. In step b) the solid residue obtained in step a) is separated from the solvent. The solid residue which does not dissolve during this alcoholic extraction is separated from the liquid by any suitable method, such as filtration or centrifugation. The solids remaining after this separation step is the basis for the further steps of the method according to the invention. Optionally a second extraction step wherein the solid material obtained after the first alcoholic extraction is brought into contact with an alcohol or any other suitable organic solvent, preferably comprising ethanol, may be carried out. The conditions of this optional second solvent extraction step are preferably similar to the first solvent extraction step a). For example the first and second solvent extraction steps are performed by contacting the vegetable material with 85% ethanol in water at 80° C., during 2.5 hours at atmospheric pressure. Atmospheric pressure means about 1.013 bar at sea level. Natural variations in the pressure may occur due to weather conditions and altitude and are within the scope of the invention.

In step c) the solid residue obtained in step b) is mixed with a buffered aqueous solution having a pH between 7 and 8, preferably during a period of between 15 minutes and 3 hours.

According to a particularly preferred embodiment the buffered aqueous solution contains (is buffered by) a weak acid or a weak base having a $pK_a$ in the range of 6.0 to 8.8, even more preferably of 6.1 to 8.5 and most preferably of 6.2 to 7.5.

Examples of weak acids/bases that may suitably used, include:

| Citrate | pK3: | 6.39 |
| Bicarbonate | pK2: | 6.35 |
| Dihydrogenphosphate | pK2 | 7.20 |
| Bisulfite | pK2 | 7.20 |
| EGCG | pK1 | 7.6 |
| Theobromine | pK | 7.89 |
| Hydroxypurine | pK | 8.26 |
| Cysteine | pK | 8.37 |

Even more preferably, said weak acids or weak bases are selected from bicarbonate, citrate, phosphate and combinations thereof, most preferably the aqueous contains bicarbonate, notably bicarbonate ions. The pH of the buffered aqueous solution may suitably be adjusted to the desired level (e.g. in the range of pH 7.0 to 8.0) by, for instance, adding potassium/sodium hydroxide and/or hydrochloric acid.

The source of the bicarbonate in step c) preferably is sodium bicarbonate or potassium bicarbonate, or combinations thereof. Hence preferably the aqueous solution comprises sodium bicarbonate or potassium bicarbonate or combinations thereof. The concentration of bicarbonate is such that the pH in this step is between 7 and 8. Preferably the pH in step c) is between 7.5 and 8. Preferably the aqueous solution is free from ammonium bicarbonate.

Preferably the temperature in step c) is between 30° C. and 100° C. at atmospheric pressure, preferably at least 60° C., preferably at least 80° C. Most preferred the temperature is at least 90° C. The extraction preferably takes place during a period of between 15 minutes and 3 hours, preferably between 30 minutes and 2 hours, most preferably between 30 minutes and 1 hour. The extraction preferably is performed at the boiling temperature of water, meaning about 100° C. at atmospheric pressure. The extraction may also be performed at a pressure higher than atmospheric pressure, potentially leading to decreased extraction time. The advantage of a higher temperature is that the extraction of the polysaccharides is more rapid than at relatively low temperatures. On the other hand, undesired side reactions are to be avoided, hence the pressure at which the reaction is performed is preferably maximally atmospheric pressure. Atmospheric pressure means about 1.013 bar at sea level. Natural variations in the pressure may occur due to weather conditions and altitude and are within the scope of the invention. Additionally at temperatures from about 70° C., endogenous enzymes present in the plant material are generally deactivated, meaning that these enzymes do not exert any activity anymore.

The vegetable material of the solid residue obtained in step b) and applied in step c) is preferably treated by using at least an amount of buffered aqueous solution which is three times more than the solid residue (w/w). More preferred the concentration of the solid residue in step c) is at least about 2% by weight of the buffered aqueous solution, more preferably at least 3% by weight. Preferably the concentration is at most 25% by weight of the buffered aqueous solution more preferably at most 15% by weight, most preferably at most 10% by weight. An advantage of a relatively low concentration of the extract in step c) is that the yield of the extraction may increase. More vegetable material comprising the polysaccharides of interest can be extracted using a relatively low concentration of residue.

The polysaccharide of interest dissolves in the aqueous solution during the mixing process in step c). Hence this solution is the material which forms the basis for further optional process steps. A solid residue may be obtained from step c), which then is the material which does not dissolve in the aqueous phase. If such a solid residue is obtained in step c), then in step d) optionally the solid residue is separated from the aqueous solution as obtained from step c). This optional separation can be done by any suitable method, such as filtration or centrifugation.

Optionally a second step like step c) can be applied to extract the polysaccharide of interest from the solid residue, if that is obtained in the first step c). In that case the preferred conditions of such a second step c) are the same as for (the first) step c). Also then a second separation step may be required, if also the second step c) would yield a solid residue. Also such an optional second aqueous extraction step may be performed without the presence of bicarbonate, meaning that only an aqueous extraction is performed.

In optional step e) finally the aqueous extract from step d) may be purified in order to concentrate the polysaccharide from the aqueous extract. This concentrating may be done by drying the extract to obtain a solid residue which contains the polysaccharide of interest. The aqueous extract may also be used as such, without concentrating or further purification. If the extract is dried, the drying method applied may involve spray drying, or vacuum evaporation, belt drying, lyophilisation, and any other suitable method.

Optionally the two or more aqueous extracts, if a second extraction step has been carried out, may be mixed to obtain a single extract containing the polysaccharide according to the invention. A dialysis step is optionally applied to the extract, in order to remove small molecules having a molecular weight below for example 10 kDa. The obtained extract after the first step is suitable to be used to modulate the immune system. Optionally coloured compounds may be removed by treatment of the extract with active coal, to absorb the coloured compounds.

An optional further process step is to add to the aqueous extract from step d) a volume of ethanol to a final concentration in the combined volume of 40% (or optionally a larger amount to 70%). After standing at about 4° C. a precipitate may be isolated containing the polysaccharide of interest. This isolation can be done by several means, e.g. centrifugation, filtration, decantation and subsequent drying giving a powder which might be subjected to additional purification methods.

The preparation obtained from the method of the invention preferably contains between 0.5% and 99% of polysaccharide by weight of the preparation, more preferably between 1% and 95% by weight of the preparation.

The polysaccharide of interest, which has been enriched in the extract obtained when performing the method according to the invention, has a backbone that comprises rhamnogalacturonan-I cores and optionally alpha(1,4)-linked homo-galacturonic acid stretches. The molar ratio of galacturonyl acid residues to rhamnosyl residues in the backbone of the polysaccharide ranges from 30:1 to 1:1. If this ratio is 1:1 then the polysaccharide contains only an RG-I core wherein galacturonic acid and rhamnose pairs are present as described before. If the ratio is larger than 1:1 then the polysaccharide contains in addition to the RG-I core also stretches of alpha(1,4)-linked homo-galacturonic acid. These stretches may be alpha(1,4)-linked polygalacturonic acid or alpha(1,4)-linked oligogalacturonic acid cores. Polygalacturonic acid is considered to be a (part of a) polymer of at least 10 galacturonyl acid residues linked to each other; oligogalacturonic acid is considered to be a (part of a) molecule of 2 to 10 galacturonyl acid residues linked to each other. The polysaccharide may comprise alternating rhamnogalacturonan-I cores and homo-galacturonic acid stretches. The polysaccharide may contain one RG-I core, with one or two homo-galacturonic acid stretches connected to either side of the RG-I core. The RG-I core may also contain at one of the ends or at both ends a single galacturonic acid residue. It may also contain more than one RG-I core, and two of these RG-I cores are connected to each other through a homo-galacturonic acid core. The exact number of RG-I cores and homo-galacturonic acid cores, and the size of the side chains that may be connected to the RG-I core will determine the molecular weight of the polysaccharide of interest.

Preferably the molar ratio of galacturonyl acid residues to rhamnosyl residues in the backbone of the polysaccharide ranges from 20:1 to 1:1, preferably from 15:1 to 1:1, preferably from 12:1 to 1.5:1, preferably from 10:1 to 2:1. Based on these ratios, it is essential that the polysaccharide comprises a RG-I core, and possibly a homo-galacturonic acid core. The polysaccharide has a molecular weight between 70 kDa and 2,000 kDa. Preferably the polysaccharide has a molecular weight between 110 kDa and 2,000 kDa, preferably between 110 kDa and 1,000 kDa, preferably between 500 kDa and 1,000 kDa.

The polysaccharide that is enriched in the preparation that is produced using the method of the invention may comprise one or more side chains attached to the RG-I core. The one or more side chains preferably comprise a backbone of at least one or more alpha(1,5)-linked arabinosyl residues and wherein the one or more side chains are substituted at the 4-OH position of the rhamnosyl residues. Said preferred side chain comprising alpha(1,5)-linked arabinosyl residues may be substantially linear or branched. In case that side chain is primarily linear, the side chain primarily comprises alpha (1,5)-linked arabinosyl residues, which form the backbone of the side chain. In case said side chain is a branched side chain, then one or more alpha-arabinosyl residues are linked to the 2-OH and/or 3-OH to the of alpha(1,5)-linked arabinans.

Alternatively the one or more side chains preferably comprise a backbone of at least one or more beta(1,4)-linked galactosyl residues and wherein said one or more side chains are substituted at the 4-OH position of the rhamnosyl residues. If the preferred polysaccharide according to the invention comprises a side chain comprising one or more beta(1,4)-linked galactan residues, then the side chain is mostly a linear unsubstituted chain. Preferably other galactans like beta(1,3)-linked galactan and/or beta(1,6)-linked galactan are absent, or at least substantially absent, which means that preferably less than 10 mol % of galactan residues are present in side chains are beta(1,3)-linked or beta(1,6)-linked galactan residues, preferably less than 5 mole %, preferably less than 2 mole %, preferably less than 1 mole %.

The polysaccharide may also comprises side chains that comprise a backbone of at least one or more alpha(1,5)-linked arabinosyl residues and wherein the one or more side chains are substituted at the 4-OH position of the rhamnosyl residues, as well as side chains that comprise a backbone of at least one or more beta(1,4)-linked galactosyl residues and wherein the one or more side chains are substituted at the 4-OH position of the rhamnosyl residues.

The preferred side chains of alpha(1,5)-linked arabinosyl residues and/or beta(1,4)-linked galactosyl residues may have various lengths. The preferred molecular weight of the preferred side chain comprising an alpha(1,5)-linked arabinosyl residues or beta(1,4)-linked galactosyl residues can be expressed as a relative number: the molar ratio between the number of arabinosyl or galactosyl residues and the number of rhamnosyl residues in the RG-I core. Preferably the molar ratio of arabinosyl residues to rhamnosyl residues is maximally 50:1, and/or the molar ratio of galactosyl residues to rhamnosyl residues is maximally 50:1. Preferably the molar ratio is smaller than this ratio, preferably the molar ratio of arabinosyl residues to rhamnosyl residues is maximally 20:1, preferably maximally 10:1, preferably maximally 5:1, preferably maximally 1:2; and/or the molar ratio of galactosyl residues to rhamnosyl residues is maximally 20:1, preferably maximally 10:1, preferably maximally 5:1, preferably maximally 1:2.

If side chains comprising arabinosyl monomers are present, the length of the side chains (expressed as number of monomer units) preferably is between 1 and 100 monomer units, more preferably between 1 and 50 units, even more preferably between 1 and 30 units.

If side chains comprising galactosyl monomers are present, the length of the side chains (expressed as number of monomer units) preferably is between 1 and 100 monomer units, more preferably between 1 and 50 units, even more preferably between 1 and 30 units.

If the polysaccharide according to the invention comprises side chains which are substituted at the 4-OH position of rhamnosyl residues of the rhamnogalacturonan-I core, then preferably at most 5% of the side chains are arabinogalactan side chains, more preferably at most 1% of the side chains are arabinogalactan side chains. This should be understood to mean that preferably the polysaccharide according to the invention is substantially free from arabinogalactan side chains, more preferably free from arabinogalactan side chains. Arabinogalactan side chains are side chains which comprise both arabinosyl and galactosyl residues. Arabinogalactan-I and arabinogalactan-II have been described above.

If the RG-I core of the polysaccharide of the invention comprises side chains, then at least 20 mole % of the rhamnosyl residues is substituted at the 4-OH position, preferably at least 30 mole %, preferably at least 40 mole %, preferably at least 45 mole %, and preferably at most 90 mole %, preferably at most 80 mole %.

In another preferred embodiment the polysaccharide that is enriched in the extract that is obtained using the method of the invention has a RG-I core that is substantially free from side chains comprising a backbone of at least one or more alpha(1,5)-linked arabinosyl residues and/or wherein the rhamnogalacturonan-I core is substantially free from side chains comprising a backbone of at least one or more alpha(1,5)-linked galactosyl residues.

In the context of the present invention, the phrase 'rhamnogalacturonan-I core is substantially free from' has to be understood as that the backbone is a straight molecule without long side chains; nevertheless still small residues of sugar monomers (like arabinose and/or galactose) may be attached to the rhamnosyl residue of the RG-I core. These residues can be stubs which may comprise 1, 2, 3, 4, 5, 6, 7, 8, 9, or 10 arabinosyl or galactosyl monomer residues. The number of these stubs per RG-I core preferably is only small, meaning less than 30 stubs per RG-I core, preferably less than 15, preferably less than 5. Hence the phrase 'rhamnogalacturonan-I core is substantially free from' can be understood to mean that the ratio between molar ratio of arabinosyl residues to rhamnosyl residues is maximally 1:10, preferably maximally 1:20; and the molar ratio of galactosyl residues to rhamnosyl residues is maximally 1:10, preferably maximally 1:20.

Preferably, in general the polysaccharide according to the invention has a small, even if any, effect on viscosity or thickening of liquid compositions when dissolved, as compared to standard pectins. With increasing molecular weight, the thickening effect preferably increases per unit weight, however this thickening effect preferably is still small. Preferably the effect as a thickener depends on the degree of branching of possible side chains and/or the average length of side chains of the RG-I core: with increasing branching and/or increasing average length of side chains, the thickening effect becomes less.

The polysaccharide according to the invention comprises residues of the monomers rhamnose, galacturonic acid, and if the polymer comprises one or more side chains, then the polysaccharide may contain residues of arabinose and/or galactose as well. In addition the polysaccharide may contain minor amounts of residues of the monomers fucose, glucose, glucuronic acid, xylose, and/or uronic acid. These monomers may for instance terminate side chains, if these are present. In a preferred embodiment the invention is directed to polysaccharides comprising xylose.

The methods for determining the structures of the polysaccharides of the present invention are known to the skilled person. These methods include analysis using $^1$H and $^{13}$C NMR.

In order to check the success of polysaccharide isolation, an overall content of carbohydrates can be determined using the Dubois method (Dubois, Analytical Chemistry, vol. 28, 1956, p. 350-356). A first rough insight in the success of removal of small oligosaccharides can be obtained by the average degree of polymerization (DP value) which is determined by comparing the analysis result on carbohydrate reducing end groups (DNSA method) with the total carbohydrate content determined by the Dubois method. Successful removal of small oligosaccharides (e.g. mono and disaccharides) would give a high average DP value (e.g. at least higher than 2). A more accurate way is to determine the molecular weight distribution of the enriched extract by size exclusion chromatography.

The optional purification of the aqueous extract in step e) preferably involves two further purification steps: first a separation of acidic compounds in the extract from non-acidic compounds; and a second optional step to separate acidic compounds into fractions having different molecular weights, to obtain the polysaccharide of interest having a molecular weight of at least 50 kDa, preferably at least 70 kDa, and maximally 2,000 kDa. In an optional first purification step the acidic fraction is separated from non-acidic compounds. The polysaccharide according to the invention contains galacturonyl acid residues in the RG-I core, and these residues make the polysaccharide according to the invention acidic. The acidic fraction can be separated from the non-acidic fraction using ion exchange. The non-acidic fraction may for instance contain neutral polysaccharides such as starch. Subsequently the acidic fraction is separated into compounds having different molecular weights, for example by gel filtration. The cut-off value of the separation on molecular weight is at 70 kDa, meaning that only molecules having a molecular weight of at least 70 kDa are retained. Preferably the cut-off is at a molecular weight of at least 110 kDa, preferably with a maximum of 2,000 kDa. The resulting material is the polysaccharide according to the first aspect of the invention. Also fractions can be made, for example a fraction of compounds having a molecular weight between 70 and 110 kDa, and more than 110 kDa. The conditions required for ion exchange and gel filtration can be determined by the skilled person.

Preferably for ion exchange anion exchange materials are used as stationary phase like strong basic resins e.g. Amberlite, Dowex and Mitshubishi (DIAION), either as gels or as beads or alternatively weak basic ion exchanger like DEAE-sepharose or WK10/WK40 of DIAION, also as beads or gels. By application of a pH, buffer (Tris, Phosphate) or salt (NaCl) concentration gradient the acidic pectin is separated from the neutral polysaccharides. Suitably, first a neutral fraction is washed off and the subsequent acidic fraction is collected, concentrated and desalted e.g. by ultrafiltration over a 10 kDa membrane or dialysis prior to GPC. Also fractionation by ion-exclusion can be used e.g. by UBK530 (ex Mitsubishi); by elution with water first the deprotonated acidic components are collected and subsequently the neutral (poly)saccharides. Preferably the gel filtration uses size exclusion materials as stationary phase e.g. Sephacryl 100-HR & 200-HR, Sephadex G-100, Superdex 200. Suitably the sample is isocratically eluted in a buffer of strength between 0.01 and 0.2 M. The size exclusion column can be calibrated by $M_W$ standards using proteins or polysaccharides. A set of dextrans is preferred to use for this.

The total amount of polysaccharides and the monosaccharide composition of the extracts can be determined by any analytical technique known to the skilled person. For both ion exchange and gel filtration the preferred detection method is by monitoring UV absorbance between 210 and 220 nm as the carboxylate groups of the compounds show absorbance in this spectral region. Other detection methods could be by Refractive index (RI), Pulse Amperometric Detection (PAD), mass spectroscopy or off line analysis of the fractions by specific saccharide detecting reactions as the sulphuric acid/phenolic method as described by Dubois.

Finally the obtained, purified extract can be dried using any suitable method, such as freeze drying, tray drying, rota-evaporation drying or spray drying.

A preferred method to obtain the polysaccharides according to the invention is as follows. A sample of a dried or fresh vegetable material, e.g. apple, carrot or bell pepper, is washed twice with 85% ethanol in water for 2.5 hours at 80° C. and once with 85% ethanol in water for 1.5 hours at 80° C. After decanting the ethanol, the pellets are dried. The polysaccharides of interest are extracted from the pellet by adding demineralised water, sodium bicarbonate to a pH between 7.5 and 8 and boiling (at about 100° C. at atmospheric pressure) for 30 to 90 minutes. After separation of dispersed material from the aqueous phase, e.g. by centrifugation, a pellet is resuspended in demineralised water containing sodium bicarbonate at a pH between 7.5 and 8, and boiled again for between 30 and 90 minutes. The supernatants of the first and second extractions are collected, freeze dried and stored at room temperature.

In a preferred subsequent step, the polysaccharide enriched freeze dried extracts are suspended at a concentration of 2% (w/w) in phosphate buffered saline (PBS) solution, and filtered clear and sterile through a 0.2 micrometer filter. As the polysaccharides according to the invention are soluble in water, the filtrate contains the polysaccharide according to the invention.

Preferably, effective separation is by using the weak ion exchange stationary phase DEAE-sepharose using a pH 7.5 Tris-HCl buffer and applying a salt gradient. The acidic fraction is desalted by ultrafiltration over a 10 kDa membrane prior to GPC and lyophilized. Subsequently the fraction is redissolved in volatile buffer (e.g. 0.1 M ammonium carbonate) and applied molecular weight distribution by size exclusion chromatography on Superdex 200 using a 5 ml/min flow. Detection by UV 214 nm absorbance and the Superdex column calibrated by dextran $M_W$ standards.

The most preferred option for some crops like carrots and apple is to skip the first column chromatography procedure and do only the size exclusion chromatography (molecular weight distribution) by gel filtration. The polysaccharide enriched extract is dissolved in volatile buffer (e.g. 0.1 M ammonium carbonate) and applied molecular weight distribution by size exclusion chromatography on Superdex 200 using a 5 ml/min flow. Detection by UV 214 nm absorbance and the Superdex column calibrated by dextran MW standards.

As the nature of the raw material from which the polysaccharides according to the invention varies, the conditions at which the optional extraction steps may be performed may vary as well. For example the amounts of solvent and water per gram of a given starting material may be different for various vegetable materials. These modifications are within the scope of the skilled person.

The molecular weight of the obtained polysaccharides is relatively high (>70 kDa), which is required to obtain a positive immuno-modulating response. The isolated fractions using the bicarbonate procedure showed a similar or better in vitro immuno-modulating activity compared to the neutral, acidic conditions. A balance can be obtained by on the one hand preventing beta-elimination to obtain polysaccharides which are relatively large, and on the other hand polysaccharides which contain both a RG-I core and polygalacturonic acid stretches in the right amount. Part of the large backbone chains in the pectic polysaccharides are degraded due to the process of beta-elimination and this can be used to influence the physical (structuring) properties of the obtained polysaccharides.

The advantages of the bicarbonate extraction over the aqueous and acid extractions as performed in the prior art are that the yield is higher, and that the proportion of polysaccharides of the total extract having a molecular weight above 70 kDa or even above 110 kDa is higher. Moreover the immuno-modulating activity of the obtained polysaccharides is at least as high as or even higher than the polysaccharides using the extraction methods of the prior art. Hence the method has the advantage that the yield of the extractions, and hence the efficiency, is higher than the methods of the prior art, and consequently using the method of the invention is advantageous as compared to the prior art methods.

Preparation Obtainable by the Method of the Invention

In a second aspect the present invention provides a preparation obtainable by the method described herein before or a preparation having a dry matter content of at least 20 wt. %, said preparation containing at least 50% by weight of dry matter of a mixture of pectic polysaccharides, including at least 20%, calculated by weight of the pectic polysaccharides, of RG-I pectins having a molecular weight of more than 40 kDa, said mixture of pectic polysaccharides being characterized by:

a degree of methylation of the galacturonyl acid residues of not more than 20%, preferably of not more than 10%;

a degree of acetylation of the galacturonyl acid residues of not more 20%, preferably of not more than 15%;
wherein the preparation does not form a gel when it is diluted with an aqueous solution of 50 mM ammoniumbicarbonate to a solids content of 2.5 wt. %. Any preferred embodiment of the method of the invention is applicable to this second aspect of the invention, mutatis mutandis.

The preparation preferably has a dry matter content of a least 40 wt. %, even more preferably of at least 80 wt. %. According to a preferred embodiment, the preparation is a dry material, e.g. a powder, having a water activity of less than 0.6, preferably of less than 0.5.

Pectic polysaccharides typically represent at least 60%, more preferably at least 70% by weight of the dry matter of the preparation. RG-I pectins having a molecular weight of more than 70-2000 kDa preferably represent at least 20%, more preferably at least 35% and most preferably 50-99%, calculated by weight of the pectic polysaccharides.

The present method offers the advantage that it yields a preparation that is largely water-soluble in water of neutral pH. Accordingly, in accordance with a preferred embodiment at least 90 wt. %, more preferably at 95 wt. % of the preparation dissolves when 25 g of the preparation is added to 1 l of distilled water having a temperature of 20° C.

The mixture of pectic polysaccharides contained in the preparation of the present invention contain a relatively small amount of methylated and/or acetylated galacturonyl residues. Preferably less than 30%, more preferably less than 20% and most preferably less than 15% of the galacturonyl acid residues in the mixture of pectic polysaccharides is methylated or acetylated.

A substantial fraction of rhamnosyl residues in the backbone of the RG-1 pectins in the preparation may be substituted at the 4-OH position with a side chain. Typically, 20-80%, more preferably 22-70% and most preferably 25-60% of the rhamnose residues contained in the preparation are substituted at the 4-OH position.

The preparation of the present invention typically contains not more than a limited amount of polysaccharides with long side chains containing alpha-(1,5)-linked arabinosyl residues. Accordingly, in a preferred embodiment the preparation has a ratio [Ara]/[Rha] of less than 20. wherein [Ara] represents the molar concentration of alpha-(1,5)-linked arabinosyl residues and [Rha] represents the molar concentration of rhamnosyl residues.

The preparation typically has a ratio [Gal]/[Rha] of 0 to 10, The wherein [Gal] represents the molar concentration of beta-(1,4)-linked galactan residues.

The ratio [GalA]/[Rha] typically is in the range of 3-20, wherein [GalA] represents the molar concentration of alpha-(1,4)-linked galacturonyl acid residue. More preferably, said ratio is in the range of 4-15.

The preparation of the present invention preferably is an extract obtained from a plant selected from apple, carrot, bell pepper, tomato, onion, ginseng, tea leaves and combinations thereof.

According to a particularly preferred embodiment, the preparation is obtainable by the method described herein before.

In a further aspect the present invention provides a preparation obtained from the method according to the first aspect of the invention or a preparation according to the second aspect of the invention for use as a medicament. Preferably the invention provides a preparation obtained from the method according to the first aspect of the invention or a preparation according to the second aspect of the invention to modulate immune response, preferably in humans. More preferably the preparation is suitable for stimulating immune response. Preferably the preparation is suitable for modulating immune response in animals or humans, more preferably in humans. A suitable method for intake of the polysaccharides or the said preparation according to the invention may be oral intake, for instance by intake of an edible product or pharmaceutical composition. Alternatively the polysaccharide or the said preparation may be taken in as ingredients in a pharmaceutical composition which is common in the field. Differences may exist between immuno-modulating effects between different animal species including humans. The immuno-modulating effects have been established using human immune cells and are therefore most pertinent to immunomodulation in humans and related mammals.

The physiological immune response of a consumer that consumes a preparation obtained from the method according to the first aspect of the invention, may be determined by ex vivo analysis of the activity of phagocytic and natural killer (NK) cells of that consumer. The immune modulating response upon ingestion of the polysaccharides according to the invention generally occurs within a few hours, e.g. 2 or 3 hours. The effect may last for about 24 hours or longer. Suitably, upon continued consumption of products containing the polysaccharide according to the invention, for example once or twice a day at consecutive days, the immune response can be stimulated and prolonged, and the natural defence of the consumer against the flu or cold can be enforced.

The daily dose of a polysaccharide that is enriched in the preparation obtained from the method of the invention, to obtain the preferred immune response modulating effect, preferably is between 1 and 10,000 milligram per day. More preferred the amount of polysaccharide dosed is between 5 and 10,000 milligram per day, preferably between 10 and 10,000 milligram per day, even more preferred between 10 and 5,000 milligram per day. More preferred the amount dosed is between 10 and 1,000 milligram per day and most preferred between 10 and 500 milligram per day. This amount may be dosed as a single dose per day, or as 2, 3, 4, 5, 6, 7, 8, 9, or 10 doses per day. Preferably the suitable amount of polysaccharides according to the invention are delivered by 1 or 2 doses per day.

The preparation for use as a medicament or for use as a medicament to modulate immune response. Such a medicament may be used in the treatment of a patient in order to recover from a disease such as the common cold, and also by a consumer to prevent from becoming ill or catching a cold. A medicament in the sense of the present invention should be explained to be a broad term, and encompasses, but is not limited to, prescription drugs, non-prescription drugs, over the counter medicines, dietary supplements, dietary foods, clinical foods, edible products, tablets, capsules, pills, and food products such as beverages or any other suitable food product, and any other composition which is commonly known to the skilled person. Alternatively the medicament may be an ointment or an injectable substance or an inhalable substance, such as a nasal spray.

Preferably the preparation obtained from the method according to the first aspect of the invention or according to the second aspect of the invention is for use in therapy or treatment. The therapy or treatment may involve not only treatment of a person in the classical sense, meaning treatment of a patient in order to recover from a disease. Treatment also includes prophylaxis, meaning preventing that a consumer becomes ill, or catches a cold or the flu. The present invention provides the use of a preparation obtained from the method according to the first aspect of the invention or according to the second aspect of the invention as a medicament. The present invention provides the use of a preparation obtained from the method according to the first aspect of the invention or according to the second aspect of the invention to modulate immune response, preferably stimulate immune response. This way individuals suffering from a cold or flu may be treated to recover earlier than without treatment, and/or this way individuals may decrease the chance that they catch a cold or the flu. The present invention provides a method for treatment of a cold or the flu or prevention against a cold or the flu by administration of the preparation obtained from the method according to the first aspect of the invention or a preparation according to the second aspect of the invention.

The preferred dosage of the polysaccharide has already been indicated.

The use of the preparation for modulating immune response may also involve veterinary use, thus modulating immune response in animals, preferably mammals.

Among the general public there is a desire to increase the natural defence of the human body against intruders which may cause a cold or the flu, or any other symptom which causes the consumer to feel weak or ill. Products obtained from the method of the invention are preferably directed to protection of a) the respiratory tract, inner and middle ear against e.g. localized and/or respiratory or middle ear infections and/or b) the gastrointestinal tract, against gastrointestinal tract infections. The infections are typically caused by viruses or bacteria. This is especially relevant for subjects with a suboptimal immune defence against such pathogens, for instance because of impaired NK cell function or production of anti-viral interferons. Impairment of these functions has been associated with increased susceptibility to such common infections and has been well documented in elderly subjects as well as in subjects experiencing physiological (e.g. strenuous exercise, shift working, sleep deprivation) or psychological (e.g. exam stress, preparing for a wedding, loss of a relative, caring for a chronically ill relative) stress.

The invention is directed to the prophylaxis of individuals in need of modulation of their immune responsiveness. The invention is especially suitable to enhance the immune response to pathogens or antigens in subjects with a (partially) suboptimal immune responsiveness due to e.g. age-, diet-, or life-style associated impairment of immune function. Application of the structures as described in the present invention can be used to support their immune system to mount an adequate response and thus increase the subject's resistance to common infections, enhance their response to a vaccine and in other applications reduce inflammatory and/or allergic conditions.

The preparation obtained from the method according to the first aspect of the invention or the preparation according to the second aspect of the invention may be used as an adjuvant for vaccines. Most vaccines in use today employ killed or attenuated microbes or microbial fragments to stimulate a protective immune response against the cognate infectious agent. However, problems associated with the manufacture of conventional vaccines has led to the development of more defined synthetic antigens using chemical and recombinant techniques. These defined antigens by themselves have a lower potency and immunogenicity and typically need to be combined with an adjuvant to form an effective vaccine. An adjuvant is an agent that stimulates the immune system and increases the response to an antigen, without having a specific antigenic effect in itself (M. Singh (ed.), Vaccine adjuvants and delivery systems, Wiley-Interscience 2007). The preparations may be combined with a specific antigen in a vaccine to increase the immune response against the antigen, in order to improve the functionality of the vaccine. For this use the antigenic material of a vaccine is combined with an amount of preparation that stimulates the initiation of a specific adaptive immune response against the specific antigen(s) without inducing overt adverse responses. Other additives as established in the field may be added to the vaccine for instance to serve as a carrier, a depot or a preservative. The preparation obtained from the method according to the first aspect of the invention or the preparation according to the second aspect of the invention may be used in vaccines for veterinary or human use and in vaccines for different application routes including vaccines that are injected (e.g. diphtheria, pertussis, tetanus, polio, smallpox, influenza, and pneumococcal polysaccharide), vaccines that are applied orally (e.g. polio, rotavirus) or that are applied nasally (e.g. influenza).

The invention revealed that the materials obtained from the method of the invention are highly active in immune modulation, preferably immune stimulation. The invention revealed that the preparations are active with regard to human immune cells (especially under conditions of examples with phagocytosis or NK cell activation), depending on the selected process, at concentrations at or below 300 microgram per milliliter, more preferably 100 microgram per milliliter, more preferably 50 microgram per milliliter, more preferably 30 microgram per milliliter, even more preferably 10 microgram per milliliter, even more preferably 3.0 microgram per milliliter, even more preferably 1.0 microgram per milliliter, even more preferably 0.3 microgram per milliliter.

Edible Product or Pharmaceutical Composition

The present invention also provides an edible product or pharmaceutical composition comprising a preparation obtained from the method according to the first aspect of the invention or a preparation according to the second aspect of the invention. Preferably the edible product or pharmaceutical composition is suitable for modulating immune response, more preferably suitable for stimulating immune response, upon intake by any suitable method.

Depending on the specific edible product or pharmaceutical composition, the edible product or pharmaceutical composition according to the invention preferably comprises from 0.0001% to 25% by weight of the preparation obtained from the method according to the first aspect of the invention or according to the second aspect of the invention, more preferred from 0.0002% to 10% by weight. Preferably the concentration of the preparation in the edible product or pharmaceutical composition according to the invention is between 0.5% and 10% by weight, preferably between 1% and 10% by weight, more preferred between 2% and 10% by weight, more preferred between 3% and 10% by weight, more preferred between 4% and 10% by weight, and most preferred between 5% and 9% by weight. The polysaccharides that is enriched in the preparation according to the invention may be present in the edible product or pharmaceutical composition in its native form, meaning as a constituent of a vegetable material which is used in the edible product or pharmaceutical composition. Nevertheless the edible product or pharmaceutical composition is also enriched with the preparation according to the invention. This means that the polysaccharide is possibly not only present in its native form as a constituent of a vegetable material, but that in addition also the polysaccharide as part of the preparation of the invention is added as an ingredient to the edible product or pharmaceutical composition.

The edible product according to the present invention may take any physical form. In particular, it may be a food product, a beverage, a dietary food product, or a clinical food product. It may also be a dietary supplement, in the form of a beverage, a tablet, a capsule, or any other suitable form for a dietary supplement. Preferred edible products for incorporation of the preparation obtained from the method according to the first aspect of the invention or according to the second aspect of the invention are in the form of a liquid, such as a soup or a beverage, a spread, a dressing, a dessert or a bread. If the preferred edible product is a soup, this may be a liquid soup, or a dried soup to which hot water can be added by the consumer. The edible product may be in liquid or spreadable form, it may be a spoonable solid or soft-solid product, or it may be a food supplement. Preferably the edible product is a liquid product. The edible product may suitably take the form of e.g. a soup, a beverage, a spread, a dressing, a dessert, a bread. More preferably, the edible product is a beverage, a dessert or a spread. More preferably, the edible product is a beverage or a spread, especially a spread in the form of an oil-in-water emulsion or a water-in-oil emulsion. The term 'spread' as used herein encompasses spreadable products such as margarine, light margarine, spreadable cheese based products, processed cheese, dairy spreads, and dairy-alternative spreads. Spreads as used herein (oil-in-water or water-in-oil emulsions) may have a concentration of oil and/or fat of between about 5% and 85% by weight, preferably between 10% and 80% by weight, more preferred between 20% and 70% by weight. Preferably the oil and/or fat are from vegetable origin (such as but not limited to sunflower oil, palm oil, rapeseed oil); oils and/or fats of non-vegetable origin may be included in the composition as well (such as but not limited to dairy fats, fish oil).

Most preferably, the product is a beverage. Such a beverage typically contains at least 60% by weight water and 0 to 20% by weight of dispersed oil or fat. Preferably, such beverage contains at least 70% by weight water and 0 to 10% by weight of dispersed oil or fat.

A dressing in the context of the present invention generally is an oil-in-water emulsion, which may contain between 0.1 and 85% of oil and/or fat. Mayonnaise is an example of a dressing within the context of the present invention. Dressings as used herein (oil-in-water emulsion) may have a concentration of oil and/or fat of between about 50.1 and 85% by weight, preferably between 5% and 80% by weight, more preferred between 10% and 70% by weight. Preferably the oil and/or fat are from vegetable origin (such as but not limited to sunflower oil, palm oil, rapeseed oil); oils and/or fats of non-vegetable origin may be included in the composition as well (such as but not limited to dairy fats, fish oil).

A pharmaceutical composition in the context of the present invention encompasses, but is not limited to, prescription drugs, non-prescription drugs, over the counter medicines, dietary supplements, dietary foods, clinical foods, edible products, tablets, capsules, pills, and food products such as beverages or any other suitable food product, and any other composition which is commonly known to the skilled person. Alternatively the medicament may be an injectable substance or an inhalable substance, such as a nasal spray. In case of a pharmaceutical composition, the composition may contain more than 25% by weight of the preparation obtained from the method according to the first aspect of the invention or according to the second aspect of the invention, preferably more than 30% by weight, preferably more than 40% by weight, or preferably more than 50% by weight, or preferably even more than 75% by weight.

Edible products suitable for this invention can be any food product, including beverages, dietary food products and clinical food products. The concentration of the preparation obtained from the method according to the first aspect of the invention or according to the second aspect of the invention should be such that modulation of the immune response occurs after consumption of the food product at a regular amount. A regular amount is the amount that an average consumer consumes of such a food product at a specific consumption moment.

The preferred daily dose of the preparation obtained from the method according to the first aspect of the invention or according to the second aspect of the invention has been indicated above, and is applicable to the fourth aspect of the invention as well. The concentration of preparation required in the edible product depends on the specific edible product and how much of such a product is usually consumed. Preferably the polysaccharides according to the invention are incorporated in edible products which are usually consumed at a predefined amount. For example a cereal bar is usually packed per single bar, and also consumed per single bar. Usually the weight of such a bar is between 40 and 80 gram. Similarly, dairy mini-drinks are consumed from small bottles, having a volume of about 100 milliliter.

By incorporating the preparation in such food products, the daily intake of the polysaccharides can in principle be controlled. Preferably the polysaccharides are delivered to the consumer in 1 or 2 doses per day. The skilled person is able to calculate the required concentration of the preparation in a unit amount of the edible product, preferably food product.

A unit amount of a food product is a quantity of a food product which is usually consumed as a single serving. The unit amount or serving size of such food products depends on the specific product. A few non-limiting examples of typical serving sizes are:

milk, yoghurt: 200 mL
natural cheese: 43 gram
processed cheese: 57 gram
fruit juice: 177 mL
soft drink: 200 mL
bread: 1 slice, 35 gram
coffee: 125 mL
tea: 150 mL
cereal bar, candy bar: 50 gram
chocolate: 30 gram
ice cream: 100 mL
spread: 15 gram
soup: 250 mL
cocoa beverage: 200 mL A unit amount of a food product in the context of the present invention may be packed and sold as a single portion. For example, ice cream may be packed as individual units, therewith making such an individual portion a unit amount in the context of the present invention. The actual weight or volume of such an individually packed product may be higher or lower than indicated above for a standard serving size. For example probiotic dairy drinks are consumed from small bottles, individually packed, having a volume of about 100 mL.

The invention also provides a method of preparing an edible product or a pharmaceutical composition said method comprising incorporating into said edible product or said pharmaceutical composition a preparation as defined herein before. According to a particularly preferred embodiment, this method yields an edible product or a pharmaceutical product as defined herein before. Typically, the method of preparing the edible product or the pharmaceutical product comprises incorporating into said edible product or said pharmaceutical product 0.5-25%, more preferably 1-20%, even more preferably 2-10%, most preferably 3-9% of the preparation. The incorporation of the preparation in the edible product or the pharmaceutically product typically comprises the step of mixing the preparation with at least one, preferably two or more other edible or pharmaceutically acceptable ingredients.

Preferred aspects disclosed in connection with either of the first, second, and third aspects of the present invention may also be applicable to the other aspects of the present invention, mutatis mutandis. The various features and embodiments of the present invention, referred to in individual sections below apply, as appropriate, to other sections, mutatis mutandis. Consequently features specified in one section may be combined with features specified in other sections, as appropriate. All publications mentioned in this specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the claims.

EXAMPLES

Figure 1:
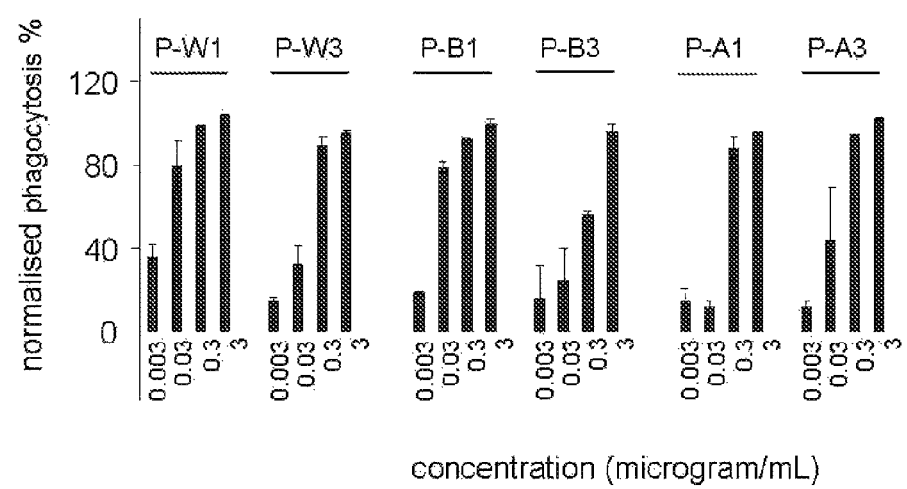
FIG. 1: Immune modulating effect of extract obtained from bell pepper, from example 2; whole blood cell assay. Concentration of extract in microgram per milliliter (x-axis) versus percentage phagocytosis (y-axis).

The following non-limiting examples describe extraction and preparation of polysaccharides obtained according to the method of the invention.

Example 1: Preparation of Vegetable Extracts

Materials and Methods
Vegetable materials used as source of the polysaccharides were dried powders:
  bell pepper (paprika, *Capsicum annuum*); Paprika Mild 80-100 (Asta St—Felix Reverte, S. A., Librilla (Murcia), Spain).
  carrot (*Daucus carota* subsp. *sativus*); ex. R. Steinicke GmbH, Breitbrunn, Germany.
  apple powders (*Malus domestica*): ex Mahevi Oy, Polyijärvi, Finland.

From the vegetable materials first alcohol insoluble residues (AIRs) were prepared by ethanol washings from these vegetable materials. The AIR materials were subjected to a set of extraction experiments in respectively water, sodium bicarbonate, or dilute hydrochloric acid.

Each vegetable material was first extracted with 80% aqueous ethanol twice (80° C., about 2 h) and then overnight at room temperature; each time using 12.5% (w/v). The insoluble residue was dried and this material is called 'alcohol insoluble residue', AIR. The AIR materials were used in all extraction experiments described here. Extractions were performed with the defined solution for specified time, and the liquid phase was recovered after centrifugation.

All extracts prepared in this sample series were dialyzed using a MWCO 6000-8000 dialysis tube to aid comparison between treatments carrying different salts. Samples (5 g insoluble residue) were twice dialyzed against about 1 liter of 50 mM ammonium bicarbonate for ca. 3-4 h and then against fresh 50 mM ammonium bicarbonate overnight, and then lyophilized.

Beside the yield, extracts were also analyzed by GPC in Superdex200 column to obtain the molecular weight profile of the extracts. In addition, the extracts were subjected to proton-NMR analysis, and the substitution pattern and composition of each extract were deduced from the spectra.

The mass % of pectin in the fractions was determined by gel-filtration chromatography on Superdex200 columns and the fraction>70 kD was found to be mainly RG-1 as confirmed by $^1$H NMR and monosaccharide hydrolysis/HPLC. The mass % of pectin could be corrected for the presence of non-pectin type monosaccharides like glucose which is indicative of the presence of starch.

Separation of Polysaccharides by Molecular Weight

Polysaccharides obtained by extraction are separated by gel filtration chromatography (GPC) on a column of Superdex 200 (1×30 cm; GE Healthcare). The polysaccharide samples are dissolved in 0.1 M ammonium bicarbonate and aliquots of 5 to 15 mg were run on the column in the same buffer. Eluting components are detected by absorption at 214 nm.

The polysaccharides are pooled into three fractions: $M_w$>110 kDa, 70-110 kDa and 40-70 kDa. The pooling limits are determined by comparing to elution positions of Dextran standards 40 kDa, 70 kDa and 110 kDa (ex GE Healthcare).

Substitution and Composition Analysis of Polysaccharides

The composition of polysaccharide fractions as obtained from the extraction process are determined using NMR analysis. Prior to NMR analysis, dry polysaccharide samples (1-10 mg) are dissolved in deuterium oxide ($D_2O$) and dried in a vacuum centrifuge. Samples are then dissolved in 600 microliter of $D_2O$, Spectra are collected on a Varian Unity 500 NMR spectrometer at 296 K and referenced to internal acetone standard (2.225 ppm).

Referring to Table 3, Table 6, and Table 9, the polysaccharide substitution level and the molar composition of the building units are analysed by using the NMR data as follows:

Rhamnogalacturonan Substitution Level

The ratio of 4-substituted rhamnosyl units and nonsubstituted units is estimated by integrating the splitted rhamnose —$CH_3$ signals. The —$CH_3$ protons in 4-substituted rhamnosyl units resonate around 1.32 ppm, while those of the nonsubstituted rhamnosyl units at 1.25 ppm.

Molar Ratio of Galactans and Arabinans

The molar amount of galactans and arabinans is analysed by integrating the observed beta-1,4-galactan H-1 signal (4.64 ppm) and the arabinan H-1 signals (-5Ara H-1, 5.09 ppm; -3,5Ara H-1 5.12 ppm; terminal Ara-alpha-1-3 5.15 ppm; terminal Ara-alpha-1-2 5.18 ppm; -2,3,5Ara H-1 5.26 ppm. These integration values are compared to the integrated rhamnose —$CH_3$ signals.

Methylation and Acetylation of Galacturonic Acid Residues

The galacturonic acid O-acetyl group —$CH_3$ signals reside around 2.07-2.18 ppm, and are integrated as no interfering signals are present in this area. The O-acetylation level is normalized to 100% being 1 acetyl group per galacturonic acid residue. The galacturonic acid methyl esterification level is estimated from the integrated galacturonic acid H-4 signals. The H-4 signal of methyl esterified galacturonic acid unit resides at 4.47 ppm, while the H-4 signal of nonesterified galacturonic acid is at 4.42 ppm.

Polygalacturonic Acid/Rhamnose Ratio

The ratio of polygalacturonic acid to rhamnose is analysed as follows: the total amount of galacturonic acid H-4 signals is integrated between 4.42 and 4.47 ppm, and the amount of rhamnose is obtained by integration of the —$CH_3$ signals (1.25-1.32 ppm). The H-4 signal of the RG-I specific GalA-alpha-1-2 unit is located in the same 4.42-4.47 signal, and its portion has to be deducted from the total H-4 signal. This value is the same as rhamnose amount, as RG-I is a 1:1 polymer of Rha and GalA. The remaining H-4 signal represents the share of polygalacturonic acid type GalA-alpha-1-4H-4 signal.

Monosaccharide Analysis (Acid Hydrolysis+HPLC)

Polysaccharide samples were dissolved in 0.5 M aqueous trifluoroacetic acid and hydrolyzed at 120° C. for 2 hours. Samples were then neutralized with NaOH, and kept frozen until analyzed by high-pH anion-exchange chromatography (HPAEC) in DX600 Ion Chromatography System (Dionex, Sunnyvale, USA) using pulsed-amperometric detection (PAD). Samples were analyzed in two different columns, CarboPacMA-1 and CarboPacPA-1 (Dionex, Sunnyvale, USA) to obtain reliable analysis of the reported monosaccharide species. The MA-1 column runs were carried out using an isocratic elution with 180 mM NaOH. PA-1 runs were carried out with the following linear gradients: minute 0-5, 50 mM NaOH, minute 5-10 from 50 to 100 mMNaOH, minute 10-35 from 0 to 200 mM NaAc in 100 mM NaOH, and minute 35-40 from 200 to 400 mM NaAc in 100-240 mM NaOH.

Extraction Methods

The following extractions of the AIR from the vegetable materials were performed:

Water extractions for 30, 60 and 90 min at 100° C. and at 70° C. Unless indicated otherwise, 10% (w/vol) suspensions were used in these experiments. The extraction with water is known in the prior art, these are comparative experiments.

Extractions with sodium bicarbonate (pH 7.5-8) were typically carried out at 7.5% (wt/vol), unless indicated otherwise. The rationale to study this extraction method was that the slightly alkaline solution could promote the degradation of the methyl esterified polygalacturonic acid chain through beta-eliminative cleavage. This would yield enriched RG-I product, as beta-elimination would be much slower for the naturally nonesterified RG-I. These are extractions according to the method of the invention.

Acid extractions were performed by hydrochloric acid at pH 2.5 and 5% (wt/vol) unless indicated otherwise, for the specified time at 70° C., after which solutions were cooled and neutralized by sodium bicarbonate. Pectin used as a gelling material in food industry is produced by acid extraction of e.g. citrus peels, followed by alcohol precipitation. It was therefore studied here whether acid extraction could produce higher amounts of RG-I also, and whether the RG-I would be stable in the acidic solution. The extraction with acid is known in the prior art, these are comparative experiments.

Extraction Efficiencies

The extraction yields, composition analysis and molecular weight distribution of the extracts obtained from the three vegetable materials, extracted using water, acid or bicarbonate are given in Table 1 to Table 9. The molecular weight distribution was measured by GPC on Superdex 200. Fractions corresponding to >110 kDa (HMW), 70-110 kDa (MMW) and 40-70 kDa (LMW) were collected and the yields measured. The remainder of the extract is considered to have a molecular weight less than 40 kDa, and this is calculated by subtracting the weight percentages of the 3 fractions from 100%. Yields are presented as weight/weight percent compared to extract injected to column. Typically 10-15 mg of extract was dissolved in about 400 microliter of running buffer. Non-dissolved material was removed before injection, and not taken into account in the calculation.

TABLE 1

Yield of extraction of bell pepper using water, acid, or bicarbonate.

| Code | Treatment | AIR starting material [g] | extraction volume [mL] | yield after extraction [g] | yield [%] |
|---|---|---|---|---|---|
| P-W1 | water 100° C., 30 min | 5.00 | 50 | 0.41 | 8.2 |
| P-W2 | water 100° C., 60 min | 5.03 | 50 | 0.44 | 8.7 |
| P-W3 | water 100° C., 90 min | 5.03 | 50 | 0.45 | 9.0 |
| P-W4 | water 70° C., 30 min | 5.00 | 50 | 0.48 | 9.5 |
| P-W5 | water 70° C., 60 min | 5.05 | 50 | 0.53 | 10.4 |
| P-W6 | water 70° C., 90 min | 5.05 | 50 | 0.46 | 9.1 |
| P-A1 | HCl 70° C., 30 min | 5.02 | 100 | 0.33 | 6.7 |
| P-A2 | HCl 70° C., 60 min | 5.00 | 100 | 0.38 | 7.6 |
| P-A3 | HCl 70° C., 90 min | 5.02 | 100 | 0.48 | 9.5 |
| P-B1 | NaHCO$_3$ 100° C., 30 min | 5.04 | 66 | 0.63 | 12.5 |
| P-B2 | NaHCO$_3$ 100° C., 60 min | 5.04 | 66 | 0.67 | 13.4 |
| P-B1 | NaHCO$_3$ 100° C., 30 min | 5.04 | 66 | 0.59 | 11.6 |

TABLE 2

Molecular weight distribution of bell pepper extracts.

| code | Treatment | $M_W$ >110 kDa [wt %] | $M_W$ 70-110 kDa [wt %] | $M_W$ >70 kDa [wt %] | $M_W$ 40-70 kDa [wt %] | $M_W$ <40 kDa [wt %] |
|---|---|---|---|---|---|---|
| P-W1 | water 100° C., 30 min | 9 | 14 | 23 | 17 | 60 |
| P-W2 | water 100° C., 60 min | 15 | 13 | 28 | 19 | 53 |
| P-W3 | water 100° C., 90 min | 12 | 16 | 28 | 21 | 51 |
| P-W4 | water 70° C., 30 min | 23 | 19.5 | 42.5 | 17 | 40.5 |
| P-W5 | water 70° C., 60 min | 11 | 15 | 26 | 11 | 63 |
| P-W6 | water 70° C., 90 min | 9 | 16 | 25 | 21 | 54 |
| P-A1 | HCl 70° C., 30 min | n.a.* | n.a. | n.a. | n.a. | n.a. |
| P-A2 | HCl 70° C., 60 min | n.a. | n.a. | n.a. | n.a. | n.a. |
| P-A3 | HCl 70° C., 90 min | n.a. | n.a. | n.a. | n.a. | n.a. |
| P-B1 | NaHCO$_3$ 100° C., 30 min | 16 | 17.5 | 33.5 | 28 | 38.5 |
| P-B2 | NaHCO$_3$ 100° C., 60 min | 13 | 13.5 | 26.5 | 23 | 50.5 |
| P-B3 | NaHCO$_3$ 100° C., 90 min | 18 | 13 | 31 | 27 | 42 |

*indicates that the extract was not run in GPC due to gel character.

TABLE 3

Composition analysis of extracts of bell pepper using water, acid, or bicarbonate.

| code | Rha subst[1] [%] | Gal/Rha[2] [mol/mol] | Ara/Rha[3] [mol/mol] | GalA OCH$_3$[4] [%] | acetylation[5] [%] | GalA/Rha[6] [mol/mol] |
|---|---|---|---|---|---|---|
| P-W1 | 25 | 0 | 4.4 | 50 | 15 | 8.5 |
| P-W2 | 30 | 0 | 10.5 | 50 | 20 | 6.8 |
| P-W3 | 30 | 0 | 4.4 | 50 | 20 | 6.9 |
| P-W4 | 20 | 0 | 16.2 | 50 | 35 | 4.8 |
| P-W5 | 15 | 0 | 3.3 | 50 | 15 | 10.0 |
| P-W6 | 20 | 0 | 6.5 | 50 | 20 | 9.2 |
| P-A1 | 35 | 0 | 3.1 | 0 | 10 | 8.1 |
| P-A2 | 40 | 0 | 5.0 | 0 | 10 | 7.3 |
| P-A3 | 35 | 0 | 5.1 | 0 | 10 | 7.1 |
| P-B1 | 30 | 0 | 0 | 0 | 5 | 13.9 |
| P-B2 | 30 | 0 | 0 | 0 | 0 | 12.1 |
| P-B3 | 45 | 0 | 0 | 0 | 0 | 5.3 |

Legend:
[1]Rha subst.: molar fraction of the Rha moieties in the RG-I core which is substituted at the C-4 position with a side chain; as measured from the Rha CH$_3$ signal shift;
[2]Gal/Rha: molar ratio of beta(1,4)-linked Gal as compared to Rha (mol/mol); relates to the length of side chains containing beta(1,4)-linked galactan residues;
[3]Ara/Rha: molar ratio of alpha(1,5)-linked arabinan as compared to Rha (mol/mol); relates to the length of side chains containing alpha(1,5)-linked arabinosyl residues;
[4]GalA OCH$_3$: degree of methylation of galacturonic acid residues (mol %);
[5]acetylation: degree of acetylation of galacturonic acid residues (mol %), 1 acetylgroup per galacturonic acid residue is set as 100%;
[6]GalA/Rha: alpha-1,4-galacturonyl acid residues vs. rhamnosyl residues (mol/mol); i.e. this number indicates the molar ratio between GalA residues in the alpha(1,4)-linked polygalacturonic acid or alpha(1,4)-linked oligogalacturonic acid cores in the polysaccharide and Rha residues in the RG-I core of the polysaccharide;

TABLE 4

Yield of extraction of carrot using water 3% (w/v), acid, or bicarbonate.

| code | Treatment | AIR starting material [g] | extraction volume [mL] | yield after extraction [g] | yield [%] |
|---|---|---|---|---|---|
| C-W1 | water 100° C., 30 min | 5.01 | 50 | 0.43 | 8.6 |
| C-W2 | water 100° C., 60 min | 5.01 | 50 | 0.25 | 5.0 |
| C-W3 | water 100° C., 90 min | 5.00 | 50 | 0.26 | 5.2 |
| C-W4 | water 100° C., 3x vol., 30 min | 1.00 | 30 | 0.14 | 14.0 |
| C-W5 | water 100° C., 3x vol., 60 min | 1.00 | 30 | 0.16 | 16.0 |
| C-W6 | water 100° C., 3x vol., 90 min | 1.07 | 30 | 0.18 | 16.4 |
| C-W7 | water 70° C., 30 min | 5.00 | 50 | 0.37 | 7.5 |
| C-W8 | water 70° C., 60 min | 5.04 | 50 | 0.42 | 8.3 |
| C-W9 | water 70° C., 90 min | 5.02 | 50 | 0.42 | 8.3 |
| C-A1 | HCl 70° C., 30 min | 5.06 | 100 | 0.65 | 12.9 |
| C-A2 | HCl 70° C., 60 min | 5.09 | 100 | 0.67 | 13.2 |
| C-A3 | HCl 70° C., 90 min | 5.04 | 100 | 0.56 | 11.2 |
| C-B1 | NaHCO$_3$ 100° C., 30 min | 5.04 | 66 | 0.86 | 17.1 |
| C-B2 | NaHCO$_3$ 100° C., 60 min | 5.04 | 66 | 0.92 | 18.2 |
| C-B3 | NaHCO$_3$ 100° C., 90 min | 5.04 | 66 | 1.03 | 20.4 |

TABLE 5

Molecular weight distribution of carrot extracts.

| code | treatment | $M_W$ >110 kDa [wt %] | $M_W$ 70-110 kDa [wt %] | $M_W$ >70 kDa [wt %] | $M_W$ 40-70 kDa [wt %] | $M_W$ <40 kDa [wt %] |
|---|---|---|---|---|---|---|
| C-W1 | water 100° C., 30 min | 9 | 16 | 25 | 22 | 53 |
| C-W2 | water 100° C., 60 min | 13 | 17.5 | 30.5 | 25.5 | 44 |
| C-W3 | water 100° C., 90 min | 13 | 18 | 31 | 25.5 | 43.5 |
| C-W4 | water 100° C., 3x vol., 30 min | 25 | 19.5 | 44.5 | 23 | 32.5 |
| C-W5 | water 100° C., 3x vol., 60 min | 26 | 22 | 48 | 29 | 23 |
| C-W6 | water 100° C., 3x vol., 90 min | 28 | 22 | 50 | 27 | 23 |
| C-W7 | water 70° C., 30 min | 15 | 24 | 39 | 24 | 37 |
| C-W8 | water 70° C., 60 min | 21 | 24 | 45 | 17 | 38 |
| C-W9 | water 70° C., 90 min | 17 | 23 | 40 | 24.5 | 35.5 |
| C-A1 | HCl 70° C., 30 min | n.a.* | n.a. | n.a. | n.a. | n.a. |
| C-A2 | HCl 70° C., 60 min | n.a. | n.a. | n.a. | n.a. | n.a. |
| C-A3 | HCl 70° C., 90 min | n.a. | n.a. | n.a. | n.a. | n.a. |
| C-B1 | NaHCO₃ 100° C., 30 min | 27 | 19.5 | 46.5 | 13 | 40.5 |
| C-B2 | NaHCO₃ 100° C., 60 min | 34 | 25 | 59 | 14 | 27 |
| C-B3 | NaHCO₃ 100° C., 90 min | 33 | 23 | 56 | 17 | 27 |

*indicates that the extract was not run in GPC due to gel character.

TABLE 6

Composition analysis of extracts of carrot using water, acid, or bicarbonate.

| code | Rha subst[1] [%] | Gal/Rha [mol/mol] | Ara/Rha [mol/mol] | GalA OCH₃ [%] | acetylation [%] | GalA/Rha [mol/mol] |
|---|---|---|---|---|---|---|
| C-W1 | 45 | 5.0 | 12.3 | 60 | 25 | 9.4 |
| C-W2 | 45 | 5.2 | 11.7 | 60 | 20 | 11.9 |
| C-W3 | 50 | 5.3 | 11.8 | 60 | 20 | 10.9 |
| C-W4 | 45 | 4.0 | 10.0 | 60 | 20 | 8.5 |
| C-W5 | 40 | 4.2 | 11.1 | 60 | 20 | 8.6 |
| C-W6 | 45 | 4.2 | 9.7 | 60 | 20 | 8.8 |
| C-W7 | 40 | 6.9 | 16.5 | 55 | 20 | 11.2 |
| C-W8 | 45 | 4.7 | 13.0 | 55 | 25 | 8.3 |
| C-W9 | 45 | 4.2 | 11.0 | 55 | 25 | 7.8 |
| C-A1 | 60 | 4.2 | 10.5 | 0 | 15 | 6.7 |
| C-A2 | 55 | 5.6 | 5.4 | 0 | 15 | 7.8 |
| C-A3 | 55 | 5.8 | 10.9 | 0 | 10 | 7.3 |
| C-B1 | 55 | 5.9 | 5.5 | 0 | 10 | 9.0 |
| C-B2 | 50 | 5.5 | 3.2 | 0 | 10 | 5.1 |
| C-B3 | 55 | 5.3 | 0.0 | 0 | 0 | 7.6 |

[1]for legend see Table 3

TABLE 7

Yield of extraction of apple using water 3.3% (w/v), acid, or bicarbonate 6.7% (w/v).

| code | treatment | AIR starting material [g] | extraction volume [mL] | yield after extraction [g] | yield [%] |
|---|---|---|---|---|---|
| A-W1 | water 100° C., 30 min | 5.01 | 50 | 0.19 | 3.8 |
| A-W2 | water 100° C., 60 min | 5.00 | 50 | 0.18 | 3.6 |
| A-W3 | water 100° C., 90 min | 5.00 | 50 | 0.15 | 3.0 |
| A-W4 | water 70° C., 30 min | 5.02 | 50 | 0.20 | 3.9 |
| A-W5 | water 70° C., 60 min | 5.01 | 50 | 0.20 | 3.9 |
| A-W6 | water 70° C., 90 min | 5.07 | 50 | 0.14 | 2.8 |
| A-A1 | HCl 70° C., 30 min | 5.06 | 75 | 0.40 | 7.9 |
| A-A2 | HCl 70° C., 60 min | 5.00 | 75 | 0.43 | 8.6 |
| A-A3 | HCl 70° C., 90 min | 5.02 | 75 | 0.47 | 9.4 |
| A-B1 | NaHCO₃ 100° C., 30 min | 5.09 | 66 | 0.73 | 14.4 |
| A-B2 | NaHCO₃ 100° C., 60 min | 5.09 | 66 | 0.48 | 9.5 |
| A-B3 | NaHCO₃ 100° C., 90 min | 5.09 | 66 | 0.40 | 8.0 |
| A-B4 | NaHCO₃ 100° C., 2.5x vol, 30 min | 1.00 | 30 | 0.10 | 10.1 |
| A-B5 | NaHCO₃ 100° C., 2.5x vol, 60 min | 1.00 | 30 | 0.097 | 9.7 |
| A-B6 | NaHCO₃ 100° C., 2.5x vol, 90 min | 1.00 | 30 | 0.13 | 12.5 |
| A-B7 | NaHCO₃ 100° C., 3x vol, 30 min | 0.50 | 20 | 0.10 | 20.4 |
| A-B8 | NaHCO₃ 100° C., 3x vol, 60 min | 0.50 | 20 | 0.11 | 22.6 |
| A-B9 | NaHCO₃ 100° C., 3x vol, 90 min | 0.52 | 20 | 0.11 | 20.7 |

TABLE 8

Molecular weight distribution of apple extracts.

| code | treatment | $M_W$ >110 kDa [wt %] | $M_W$ 70-110 kDa [wt %] | $M_W$ >70 kDa [wt %] | $M_W$ 40-70 kDa [wt %] | $M_W$ <40 kDa [wt %] |
|---|---|---|---|---|---|---|
| A-W1 | water 100° C., 30 min | 13 | 4 | 17 | 28.5 | 54.5 |
| A-W2 | water 100° C., 60 min | 6 | 12 | 18 | 24 | 58 |
| A-W3 | water 100° C., 90 min | 17 | 24 | 41 | 30 | 29 |
| A-W4 | water 70° C., 30 min | 8 | 12 | 20 | 14 | 66 |
| A-W5 | water 70° C., 60 min | 11.5 | 11.5 | 23 | 20.5 | 56.5 |
| A-W6 | water 70° C., 90 min | 11.5 | 13 | 24.5 | 12.5 | 63 |
| A-A1 | HCl 70° C., 30 min | n.a.* | n.a. | n.a. | n.a. | n.a. |
| A-A2 | HCl 70° C., 60 min | n.a. | n.a. | n.a. | n.a. | n.a. |
| A-A3 | HCl 70° C., 90 min | n.a. | n.a. | n.a. | n.a. | n.a. |
| A-B1 | NaHCO$_3$ 100° C., 30 min | 26 | 19.5 | 45.5 | 15.5 | 39 |
| A-B2 | NaHCO$_3$ 100° C., 60 min | 22.5 | 12.5 | 35 | 11.5 | 53.5 |
| A-B3 | NaHCO$_3$ 100° C., 90 min | 32 | 19 | 51 | 13 | 36 |
| A-B4 | NaHCO$_3$ 100° C., 2.5x vol, 30 min | 22 | 9 | 31 | 14 | 55 |
| A-B5 | NaHCO$_3$ 100° C., 2.5x vol, 60 min | 20 | 8 | 28 | 13.5 | 58.5 |
| A-B6 | NaHCO$_3$ 100° C., 2.5x vol, 90 min | 22 | 12 | 34 | 13 | 53 |
| A-B7 | NaHCO$_3$ 100° C., 3x vol, 30 min | 17 | 9 | 26 | 13 | 61 |
| A-B8 | NaHCO$_3$ 100° C., 3x vol, 60 min | 15 | 10 | 25 | 13 | 62 |
| A-B9 | NaHCO$_3$ 100° C., 3x vol, 90 min | 29 | 10.5 | 39.5 | 14 | 46.5 |

*indicates that the extract was not run in GPC due to gel character.

TABLE 9

Composition analysis of extracts of apple using water, acid, or bicarbonate.

| code | Rha subst[(1)] [%] | Gal/Rha [mol/mol] | Ara/Rha [mol/mol] | GalA OCH$_3$ [%] | acetylation [%] | GalA/Rha [mol/mol] |
|---|---|---|---|---|---|---|
| A-W1 | 35 | 0.0 | 16.8 | 50 | 10 | 10.6 |
| A-W2 | 40 | 0.0 | 20.3 | 50 | 15 | 9.2 |
| A-W3 | 40 | 1.4 | 23.2 | 55 | 15 | 8.9 |
| A-W4 | 30 | 2.7 | 19.7 | 50 | 15 | 8.1 |
| A-W5 | 40 | 0.0 | 19.1 | 50 | 15 | 7.8 |
| A-W6 | 25 | 0.0 | 18.6 | 50 | 20 | 6.5 |
| A-A1 | 50 | 3.2 | 33.5 | 0 | 10 | 12.3 |
| A-A2 | 50 | 2.2 | 24.3 | 0 | 5 | 13.7 |
| A-A3 | 50 | 2.1 | 28.5 | 0 | 5 | 13.7 |
| A-B1 | 55 | 0.0 | 7.6 | 0 | 5 | 12.0 |
| A-B2 | 55 | 0.0 | 3.8 | 0 | 0 | 11.9 |
| A-B3 | 50 | 0.0 | 6.9 | 0 | 0 | 7.5 |
| A-B4 | 45 | 0.0 | 15.0 | 5 | 5 | 9.4 |
| A-B5 | 40 | 0.0 | 13.8 | 0 | 0 | 8.7 |
| A-B6 | 45 | 0.0 | 11.7 | 0 | 0 | 7.1 |
| A-B7 | 40 | 0.0 | 11.3 | 0 | 0 | 6.4 |
| A-B8 | 40 | 0.0 | 11.8 | 0 | 0 | 6.4 |
| A-B9 | 45 | 0.0 | 11.7 | 0 | 0 | 6.7 |

[(1)]for legend see Table 3

Extractions (Table 1, Table 4, Table 7)

Bell pepper: highest extraction yields were obtained with the extractions using bicarbonate, as compared to extractions using water or acid. The yields were on average 2 to 3% higher than those obtained with water. The temperature of the water extraction did not have much influence. Also with carrot or apple as vegetable material, the use of bicarbonate yielded most extracts, as compared to extractions using water or acid.

In case of carrot, the extraction yields at 100° C. are lower after 60 and 90 min than at 30 min. This can be explained by the extraction solution that after 60 min was much more viscous than at 30 min, and part of the extracted polysaccharides are not recovered but stay in the gel. This behavior was not observed at 70° C., and neither at the bicarbonate extractions. The formation of gel seems to be concentration dependent, as extractions at 100° C. at three-fold dilution (samples C-W4, C-W5, C-W6) did not show the reduction in yield.

Also in case of apple that were extracted using bicarbonate (samples A-B1, A-B2, A-B3), a decrease in yield was observed with increasing extraction time. Also in this case some gelling occurred. Extractions at lower concentrations of the AIR revealed that the drop in yield with increasing extraction time could be prevented.

Molecular Weight Distribution (Table 2, Table 5, Table 8)

With bell pepper as vegetable material, the molecular weight distribution of the materials extracted using bicarbonate was more to the higher end of the molecular weights. As compared to extraction using water only, the bicarbonate extractions during 60 and 90 minutes (samples P-B2, P-B3) yielded a higher proportion of material with a molecular weight above 70 kDa than the extractions with water (samples P-W1 to P-W6).

Also in case of carrot as source material, the proportion of polysaccharides having a molecular weight above 70 kDa extracted using bicarbonate during at least 60 minutes was higher than the corresponding extractions with water. The >110 kDa material was the major component in the fractions extracted using bicarbonate.

The extractions of apple using bicarbonate also led to a higher proportion of polysaccharides having a molecular weight above 70 kDa as compared to extractions with water. Dilution of the vegetable material during the bicarbonate extractions did not lead to improved yield of the polysaccharides of interest. The >110 kDa fraction is dominating in all the apple samples extracted using bicarbonate. This fraction is expected to give the best immuno-modulating results. By using bicarbonate the extraction yield can be increased, without giving in on immuno-modulation.

The viscosity of extracts obtained using acid was too high to be able to determine the molecular weight distribution. This shows that acid extraction of these vegetable materials was not a suitable method to isolate the polysaccharides of interest.

Compositions of the Extracts (Table 3, Table 6, Table 9)

The extracts obtained contain RG-I fragments which have been released from the polysaccharides in the vegetable materials. If the ratio GalA/Rha is 1, then an extract contains only an RG-I core. If the ratio GalA/Rha is larger than 1, then in addition to the RG-I core, stretches of homogalacturonic acid stretches are attached to the RG-I core. The RG-I core usually contains side chains of mainly arabinan and galactan, which are attached to the rhamnose residues.

Bell pepper: the bicarbonate extracts have a higher share of polygalacturonic acid (GalA/Rha) than water extracts. An explanation for this may be that in the bicarbonate solution de-esterification is more rapid than beta-elimination, which actually decreases the polygalacturonic acid chain cleavage.

Carrot: the extracts prepared using water extraction at 100° C. (samples C-W1, C-W2, C-W3) are practically identical with regard to amount of Gal and Ara in the side chain of the RG-I polysaccharide. Samples obtained at 70° C. (C-W7, C-W8, C-W9) contain somewhat larger side chains, especially the ratio Ara/Rha is larger. The extractions with bicarbonate lead to reduction of the side chains of the RG-I polysaccharides, as the ratio Gal/Rha and Ara/Rha decrease with increasing extraction times.

Apple: the samples extracted using bicarbonate show that galactan in side chains was not detected anymore, while in case of acid and water extractions, some of the extracts still some galactan in the side chains can be detected. Also the amount of arabinan in the side chains decreases due to the extractions with bicarbonate. The extracts obtained from diluted samples (A-B4 to A-B9) show that higher-volume extractions seem to produce, on average, slightly higher arabinan ratio and lower polygalacturonic acid share than the extracts obtained from non-diluted samples (A-B1 to A-B3).

For all three crops studied here, the acidic extractions led to viscous solutions, for which it was not possible to determine molecular weight distribution. This may reflect a high amount of polygalacturonic acid which is in the extract (i.e. a high ratio of GalA/Rha), although NMR data does not prove this assumption. However, as NMR analysis does not tolerate particulate matter in the tube, the routine is to centrifuge the samples, and thus the NMR analysis of these extracts may be biased as gel-type of material was also lost.

Example 2: Immuno-Modulating Activity of the Vegetable Extracts

A whole blood assay has been used to determine the in vitro immunomodulating response of the extracts obtained from the methods as described in example 1. This assay is based on phagocytosis activity.

Phagocytosis activity in whole blood is evaluated using the Phagotest® kit of Orpegen Pharma (Heidelberg, Germany) using an adjusted protocol. Fresh blood is obtained from healthy human volunteers in sodium heparin vacutainers (BD Biosciences). 30 microliter of whole blood and 5 microliter of the ingredient are incubated in duplicates for 30 minutes in a polypropylene 96-well plate at 37° C. in a water bath. Control incubations consisted of PBS (=basal phagocytosis activity) or 100 ng/mL $E.$ $coli$-lipopolysaccharide (LPS) (=positive control sample) in triplicate measurements. After the incubation step, 10 microliter of FITC-labeled $E.$ $coli$ (white blood cell to $E.$ $coli$ ratio of 25:1) is added. This incubation at 37° C. is stopped after 6.5 minutes by adding 50 microliter of ice-cold quencher solution. The cells are washed three times by adding 230 microliter of ice-cold wash-buffer and centrifugation for 3 min at 300 g (4° C.). The erythrocytes are lysed using 290 microliter of lysis buffer. After incubation in the dark for 20 minutes at room temperature, the cells are centrifuged for 5 min at 300 g (4° C.). Cells are resuspended in 150 microliter of wash-buffer and stained with propidium iodide. Analysis is performed by flow cytometry (Coulter FC500MPL flow cytometer, Beckman Coulter Nederland BV, Mijdrecht). Within the leucocytes, granulocytes are gated according to the FSC/SSC profile. The percentage of phagocytosing cells in the granulocyte population is determined. The results are normalized to the dynamic range between basal and LPS-stimulated phagocytosis and expressed as a relative percentage phagocytosis activity. A normalized percentage of more than 40% is considered to be positive. This assay gives an estimation of the immunomodulating activity, trends can be observed from this. All samples were passed over a preconditioned C-18 cartridge before application to the immuno measurement.

The following extracts were tested in the assay:

| | | |
|---|---|---|
| P-W1 | bell pepper | water 100° C., 30 min |
| P-W3 | bell pepper | water 100° C., 90 min |
| P-A1 | bell pepper | HCl 70° C., 30 min |
| P-A3 | bell pepper | HCl 70° C., 90 min |
| P-B1 | bell pepper | NaHCO$_3$ 100° C., 30 min |
| C-W1 | carrot | water 100° C., 30 min |
| C-W3 | carrot | water 100° C., 90 min |
| C-A1 | carrot | HCl 70° C., 30 min |
| C-A3 | carrot | HCl 70° C., 90 min |
| C-B1 | carrot | NaHCO$_3$ 100° C., 30 min |
| C-B3 | carrot | NaHCO$_3$ 100° C., 90 min |
| A-W1 | apple | water 100° C., 30 min |
| A-W3 | apple | water 100° C., 90 min |
| A-A1 | apple | HCl 70° C., 30 min |
| A-A3 | apple | HCl 70° C., 90 min |
| A-B1 | apple | NaHCO$_3$ 100° C., 30 min |
| A-B3 | apple | NaHCO$_3$ 100° C., 90 min |

Figure 2:
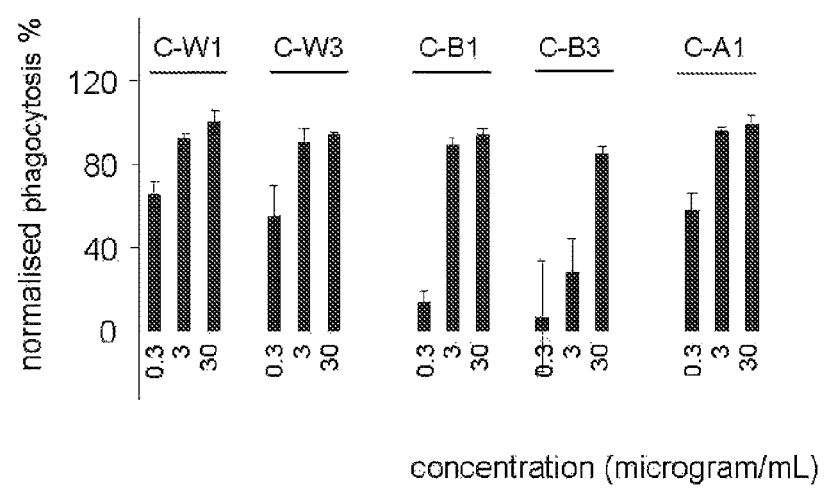
FIG. 2: Immune modulating effect of extract obtained from carrot, from example 2; whole blood cell assay. Concentration of extract in microgram per milliliter (x-axis) versus percentage phagocytosis (y-axis).
Figure 3:
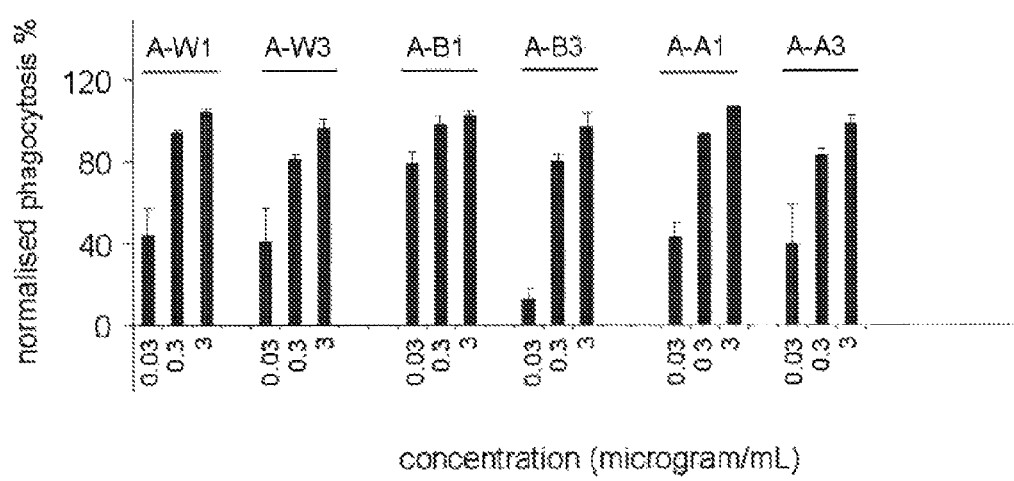
FIG. 3: Immune modulating effect of extract obtained from apple, from example 2; whole blood cell assay. Concentration of extract in microgram per milliliter (x-axis) versus percentage phagocytosis (y-axis).

The measured phagocytosis data of these extracts are given in FIG. 1, FIG. 2, and FIG. 3.

The extracts obtained from bell pepper showed already some phagocytosis activity at a concentration as low as 0.003 microgram per mL (FIG. 1). The extract obtained using bicarbonate at 30 min (P-B1) showed similar activity as the extract obtained using water at 100° C. at 30 min (P-W1). Also the activity of the bicarbonate sample as compared to acid extraction had improved. The activity of the 30 min samples was higher than the 90 min samples, especially at the low concentrations of the extract (0.3 microgram per mL and less).

Monosaccharide analysis showed that Ara and Gal could not be detected anymore in the bicarbonate samples (P-B1, P-B3). Hence in these extracts, side chains are not required to stimulate phagocytosis.

With carrot as vegetable material, the extracts obtained using bicarbonate were similarly active as the water extracts at an extract concentration of 30 microgram per mL. The bicarbonate extract obtained at 30 minutes extraction was more active than the 90 minute extract.

When comparing the monosaccharide compositions of the extracts, for the bicarbonate extracts (C-B1, C-B3), the ratio Ara/Rha in the side chains is lower than for the water extracts (A-W1, A-W3), and the ratio GalA/Rha is lower than for the water samples. This shows that the extract obtained from carrot using bicarbonate is richer in RG-I core with a smaller amount of homogalacturonic acid residues attached to the RG-I core than the water extract, while the side chains of the RG-I core contain less Ara.

In case of apple, the activity of the 30 minute bicarbonate sample (A-B1) was higher than the water (A-W1) and acid (A-A1) samples. The 90 minute samples were similar in activity. Also here the ratio of Ara/Rha of the bicarbonate extracts is lower than the water extracts. In both cases the Gal/Rha ratio is very low or zero.

CONCLUSIONS

These results show that the extracts obtained using bicarbonate possess immuno-modulating activity as they are active in the whole blood assay. The ratio of GalA/Rha of the tested extracts ranges from about 5 and 14, and these extracts showed phagocytosis activity. This shows that the RG-I core may contain attached homogalacturonic acid stretches of various lengths. Some of the side chains of the RG-I core are very low in Ara and/or Gal, meaning that these side chains are not specifically required for immuno-stimulating activity.

The combination of relatively high yield of the extracts using bicarbonate as compared to water and acid extractions, combined with the activity of the extracts in the in vitro assays, show that the method of the invention is advantageous to obtain the extract containing polysaccharides that modulate immune response.

The invention claimed is:

1. A method of preparing a food or pharmaceutical composition, comprising incorporating into the composition 0.5-25 wt. % of polysaccharide preparation isolated from a vegetable material selected from apple, carrot, bell pepper, tomato, onion, or combinations thereof enriched in rhamnogalacturonan-1 (RG-1) polysaccharide with a backbone comprising rhamnogalacturonan-I cores and optionally alpha(1,4)-linked homo-galacturonic acid stretches, wherein the molar ratio of galacturonyl acid residues to rhamnosyl residues in the backbone of the RG-1 polysaccharide ranges from 10:1 to 1:1, and wherein the RG-1 polysaccharide has a molecular weight between 40 kDa and 2,000 kDa;
wherein the pectic polysaccharides contained in the polysaccharide preparation comprise at least 20 wt. % of the RG-I polysaccharide,
wherein the polysaccharide preparation does not form a gel when diluted with an aqueous solution of 50 mM ammonium bicarbonate to a solids content of 2.5 wt. %, and
wherein at least 90 wt. % of the polysaccharide preparation dissolves when 25 g of the polysaccharide preparation is added to 1 liter of distilled water having a temperature of 20° C.

2. The method according to claim 1, wherein at least 95 wt. % of the polysaccharide preparation dissolves when 25 g of the polysaccharide preparation is added to 1 liter of distilled water having a temperature of 20° C.

3. The method according to claim 1, wherein less than 30% of the galacturonyl acid residues in the polysaccharide is methylated or acetylated.

4. The method according to claim 1, wherein the polysaccharide preparation has a ratio [Ara]/[Rha] of less than 20, wherein [Ara] represents the molar concentration of alpha-(1,5)-linked arabinosyl residues and [Rha] represents the molar concentration of rhamnosyl residues.

5. The method according to claim 1, wherein the vegetable material is selected from selected from apple, carrot, bell pepper, or combinations thereof.

6. The method according to claim 1, wherein the polysaccharide preparation has a water activity of less than 0.6.

7. The method according to claim 1, wherein the polysaccharide preparation is obtained by:
(a) mixing the vegetable material with a polar alcoholic solvent to provide a solid residue;
(b) separating the solid residue obtained in step (a) from the solvent;
(c) mixing the solid residue obtained in step (b) with a buffered aqueous solution having a pH between 7 and 8; and
(d) isolating the polysaccharide preparation from the buffered aqueous solution;
(e) optionally separating the solid residue from the aqueous solution of step (c); and
(f) optionally concentrating the aqueous solution from step (d) to provide the isolated polysaccharide preparation.

8. The method according to claim 7, wherein the polar alcoholic solvent is ethanol.

9. The method according to claim 7, wherein the buffered aqueous solution comprises a weak acid or a weak base having a $pK_a$ in the range of 6.0 to 8.8.

10. The method according to claim 7, wherein the mixing in step (c) is performed at a temperature between 30° C. and 100° C. and at atmospheric pressure.

11. The method according to claim 10, wherein the temperature is between 60° C. and 100° C.

12. The method according to claim 7, wherein cell walls in the vegetable material have been destructed.

13. The method according to claim 7, wherein the vegetable material is mixed with a total amount of the polar alcoholic solvent that is at least 8 times higher than the dry weight of the vegetable material.

14. The method according to claim 7, wherein the vegetable material is mixed with the polar alcoholic solvent and optionally water to produce a mixture containing the polar alcoholic solvent and the water in a weight ratio that is within the range of 1:1 to 19:1.

15. The method according to claim 7, wherein the polar alcoholic solvent is a C1-4 alcohol.

16. The method according to claim 7, wherein the solid residue is mixed with the aqueous buffering solution in a weight ratio of 2:100 to 25:100.

17. The method according to claim 7, wherein the molar ratio of galacturonyl acid residues to rhamnosyl residues in the backbone of the polysaccharide ranges from 20:1 to 1:1.

18. The method according to claim 7, wherein the polysaccharide has a molecular weight between 50 kDa and 2,000 kDa.

19. The method according to claim 18, wherein the polysaccharide has a molecular weight between 70 kDa and 2,000 kDa.

20. The method according to claim 1, wherein the polysaccharide preparation is obtained by:
(a) mixing the vegetable material with 85% ethanol at 80° C. for 2.5 h to provide a solid residue;
(b) separating the solid residue obtained in step (a) from the ethanol;
(c) mixing the solid residue obtained in step (b) with $NaHCO_3$ solution at 100° C. for 60 min;
(d) separating the solid residue from the $NaHCO_3$ solution as obtained from step (c); and
(d) isolating the polysaccharide preparation from the $NaHCO_3$ solution;
(f) optionally repeating steps (c) and (d); and
(g) centrifuging the $NaHCO_3$ solution in step (d) to provide the isolated polysaccharide preparation.

21. The method according to claim 1, wherein less than 20% of the galacturonyl acid residues in the polysaccharide are methylated or acetylated.

* * * * *